United States Patent
Imada et al.

(10) Patent No.: US 10,105,673 B2
(45) Date of Patent: Oct. 23, 2018

(54) TREATMENT LIQUID PRODUCTION DEVICE AND TREATMENT LIQUID PRODUCTION METHOD

(71) Applicant: Panasonic Intellectual Property Management Co., Ltd., Osaka (JP)

(72) Inventors: Katsumi Imada, Nara (JP); Mariko Miyashita, Hyogo (JP); Yoshiko Miyamoto, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 241 days.

(21) Appl. No.: 14/723,504

(22) Filed: May 28, 2015

(65) Prior Publication Data

US 2015/0352516 A1 Dec. 10, 2015

(30) Foreign Application Priority Data

Jun. 6, 2014 (JP) .................. 2014-117686

(51) Int. Cl.
*B01J 19/08* (2006.01)
*A61L 9/22* (2006.01)
(Continued)

(52) U.S. Cl.
CPC .............. *B01J 19/088* (2013.01); *A61L 2/00* (2013.01); *A61L 9/00* (2013.01); *A61L 9/22* (2013.01);
(Continued)

(58) Field of Classification Search
CPC .............. B01J 19/088; B01J 2219/0809; B01J 2219/0813; B01J 2219/083;
(Continued)

(56) References Cited

U.S. PATENT DOCUMENTS 5,630,915 A * 5/1997 Greene .................. B01J 19/088
204/164
2014/0014516 A1 1/2014 Kumagai et al.
(Continued)

FOREIGN PATENT DOCUMENTS

JP 2005-058886 3/2005
JP 2007-207540 8/2007
(Continued)

*Primary Examiner* — Xiuyu Tai
(74) *Attorney, Agent, or Firm* — McDermott Will & Emery LLP

(57) ABSTRACT

A treatment liquid production device includes a first tank; a first plasma generating device that includes a first pair of electrodes and a first power supply, the first power supply applying a voltage between the first pair of electrodes, the first plasma generating device generating plasma in a liquid in the first tank; a second tank; a second plasma generating device that includes a second pair of electrodes and a second power supply, the second power supply applying a voltage between the second pair of electrodes, the second plasma generating device generating plasma in a liquid in the second tank; and a controller operative to produce a first treatment liquid having a high initial oxidizing power during a first period and a second treatment liquid having a high remaining oxidizing power during a second period which is longer than the first period.

8 Claims, 17 Drawing Sheets

(51) Int. Cl.
*C02F 1/46* (2006.01)
*A61L 2/00* (2006.01)
*A61L 9/00* (2006.01)
*C02F 1/461* (2006.01)

(52) U.S. Cl.
CPC .......... *C02F 1/4606* (2013.01); *C02F 1/4608* (2013.01); *B01J 2219/083* (2013.01); *B01J 2219/0809* (2013.01); *B01J 2219/0813* (2013.01); *B01J 2219/0841* (2013.01); *B01J 2219/0877* (2013.01); *B01J 2219/0884* (2013.01); *B01J 2219/0894* (2013.01); *C02F 2001/46138* (2013.01); *C02F 2303/04* (2013.01); *C02F 2305/023* (2013.01)

(58) Field of Classification Search
CPC ........ B01J 2219/0841; B01J 2219/0877; B01J 2219/0884; B01J 2219/0894; A61L 2/00; A61L 9/00; A61L 9/22; C02F 1/4606; C02F 1/4608; C02F 2001/46138; C02F 2303/04; C02F 2305/023; C02F 1/46109; C02F 1/32; C02F 1/34; C02F 11/00; C02F 11/12; C02F 2201/4615; C02F 2201/46175

See application file for complete search history.

(56) References Cited

U.S. PATENT DOCUMENTS

2014/0231329 A1  8/2014  Imai et al.
2015/0102255 A1  4/2015  Imai et al.

FOREIGN PATENT DOCUMENTS

| JP | 2009-255027 | 11/2009 |
| WO | 2012/157248 | 11/2012 |
| WO | 2014/017020 | 1/2014 |
| WO | 2014/171138 | 10/2014 |

\* cited by examiner

TREATMENT LIQUID PRODUCTION DEVICE AND TREATMENT LIQUID PRODUCTION METHOD

BACKGROUND

1. Technical Field

The present disclosure relates to a treatment liquid production device which produces a treatment liquid electrochemically. More particularly, the present disclosure relates to a treatment liquid production device which produces a treatment liquid by generating plasma in a liquid. Hereinafter, treating a liquid by generating plasma will be referred to as "plasma treatment".

2. Description of the Related Art

As a conventional liquid treatment device using high-voltage pulse discharge, for example, a sterilization device disclosed in Japanese Unexamined Patent Application Publication No. 2009-255027 is known. FIG. 19 illustrates a configuration of the sterilization device.

A sterilization device 1 includes, as discharge electrodes 6, a high-voltage electrode section 5 and a ground electrode 3. The high-voltage electrode section 5 is configured with a high-voltage electrode 2, which has a columnar shape, and an insulator 4, which covers the high-voltage electrode 2 except an end face of a tip portion 2a. The tip portion 2a of the high-voltage electrode 2 and the ground electrode 3 are arranged in such a way as to be dipped in target treatment water 8 in a treatment tank 7, have a predetermined space therebetween, and face each other. The high-voltage electrode 2 and the ground electrode 3 are connected to a power supply 9, which generates a high-voltage pulse. By the power supply 9, a negative high-voltage pulse of 2 to 50 kV/cm and 100 Hz to 20 kHz is applied to the high-voltage electrode 2 and discharged. At this time, due to energy of the applied electric power, gas bubbles 10 and jets 11 are generated. Plasma is also generated around the high-voltage electrode 2, causing active species, such as OH, H, O, $O_2^-$, $O^-$, and $H_2O_2$, to be generated. These active species kill microorganisms and bacteria.

SUMMARY

In the above-described conventional technology, a further improvement in oxidizing ability of a treatment liquid has been expected.

One non-limiting and exemplary embodiment provides a treatment liquid production device and a treatment liquid production method which make it possible to improve oxidizing ability of a treatment liquid.

In one general aspect, the techniques disclosed here feature a treatment liquid production device that include a first tank; a first plasma generating device that includes a first pair of electrodes and a first power supply, the first power supply applying a voltage between the first pair of electrodes, the first plasma generating device generating plasma in a liquid in the first tank; a second tank; a second plasma generating device that includes a second pair of electrodes and a second power supply, the second power supply applying a voltage between the second pair of electrodes, the second plasma generating device generating plasma in a liquid in the second tank; and a controller operative to: cause the first plasma generating device to generate plasma during a first period to produce a first treatment liquid in the first tank; and cause the second plasma generating device to generate plasma during a second period to produce a second treatment liquid in the second tank, the second period being longer than the first period, an initial oxidizing power of the first treatment liquid being higher than an initial oxidizing power of the second treatment liquid, a remaining oxidizing power of the second treatment liquid being higher than a remaining oxidizing power of the first treatment liquid.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
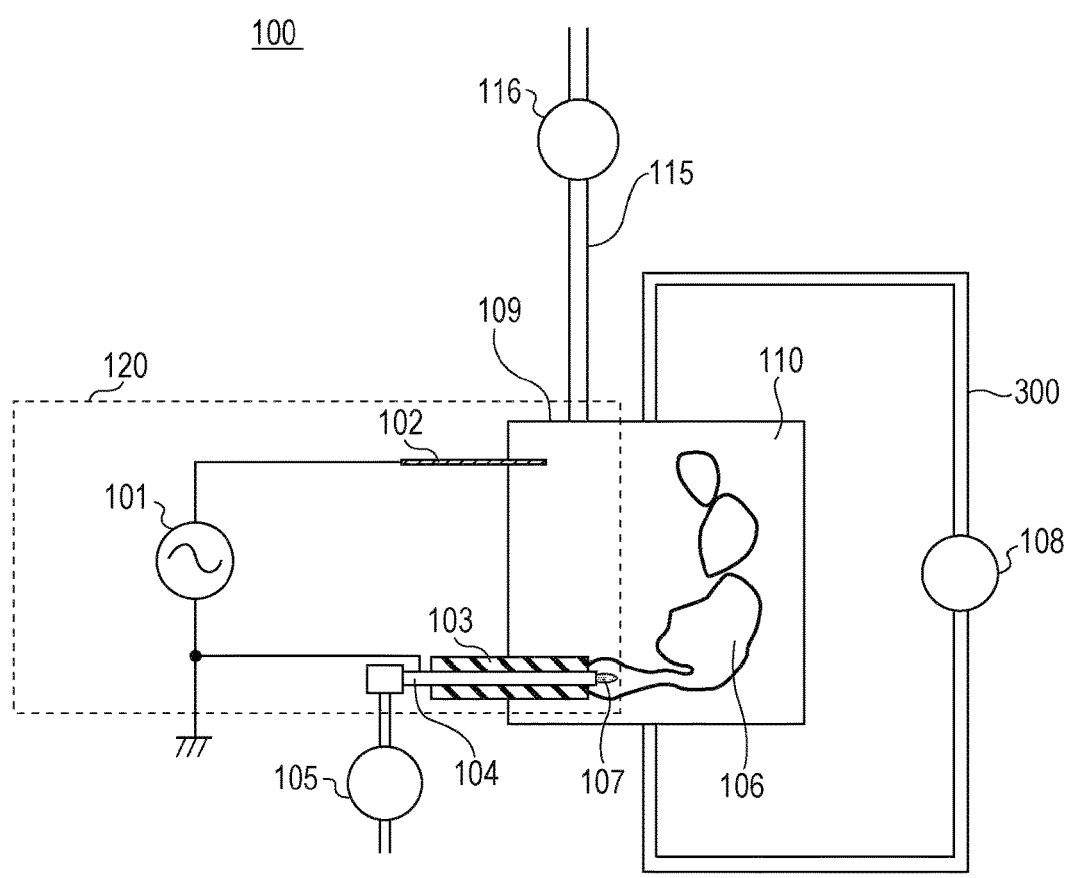
FIG. 1 is an overall configuration diagram illustrating a treatment liquid production unit.

Embodiments of the present disclosure are summarized as follows.

(1) a treatment liquid production device that include a first tank; a first plasma generating device that includes a first pair of electrodes and a first power supply, the first power supply applying a voltage between the first pair of electrodes, the first plasma generating device generating plasma in a liquid in the first tank; a second tank; a second plasma generating device that includes a second pair of electrodes and a second power supply, the second power supply applying a voltage between the second pair of electrodes, the second plasma generating device generating plasma in a liquid in the second tank; and a controller operative to: cause the first plasma generating device to generate plasma during a first period to produce a first treatment liquid in the first tank; and cause the second plasma generating device to generate plasma during a second period to produce a second treatment liquid in the second tank, the second period being longer than the first period, an initial oxidizing power of the first treatment liquid being higher than an initial oxidizing power of the second treatment liquid, a remaining oxidizing power of the second treatment liquid being higher than a remaining oxidizing power of the first treatment liquid.

(2) According to a specific aspect, in the treatment liquid production device according to the description (1) above, the first period may be substantially identical to a time at which, on a graph that indicates a relation between a plasma treatment time of the first plasma generating device and the initial oxidizing power of the first treatment liquid, the initial oxidizing power is a maximum value at a peak. The second period may be identical to a time at which, on a graph that indicates a relation between a plasma treatment time of the second plasma generating device and the initial oxidizing power of the second treatment liquid, the initial oxidizing power is a substantially saturated value.

(3) A treatment liquid production device, which is another aspect of the present disclosure, includes a first tank; a plasma generating device that includes a pair of electrodes and a power supply, the power supply applying a voltage between the pair of electrodes, the plasma generating device generating plasma in a liquid in the first tank; a second tank; a connection flow path that connects the first tank and the second tank; a connection pump provided to the connection flow path; and a controller operative to: cause the plasma generating device to generate plasma during a second period to produce a second treatment liquid in the first tank; cause the connection pump to move the second treatment liquid in the first tank to the second tank via the connection flow path; and cause the plasma generating device to generate plasma during a first period to produce a first treatment liquid in the first tank, the first period being longer than the second period, an initial oxidizing power of the first treatment liquid being higher than an initial oxidizing power of the second treatment liquid, a remaining oxidizing power of the second treatment liquid being higher than a remaining oxidizing power of the first treatment liquid.

(4) According to a specific aspect, in the treatment liquid production device according to the description (3) above, the first period may be substantially identical to a time at which, on a graph that indicates a relation between a plasma treatment time of the plasma generating device and the initial oxidizing power of the first treatment liquid, the initial oxidizing power is a maximum value at a peak. The second period may be identical to a time at which, on a graph that indicates a relation between the plasma treatment time of the plasma generating device and the initial oxidizing power of the second treatment liquid, the initial oxidizing power is a substantially saturated value.

(5) According to a specific aspect, the treatment liquid production device according to any one of the descriptions (1) to (4) above may further include a discharge flow path connected to the first tank and the second tank; and at least one discharge pump provided to the discharge flow path. The at least one discharge pump may discharge the first treatment liquid in the first tank and the second treatment liquid in the second tank to the outside via the discharge flow path. The controller may cause the at least one discharge pump to discharge the first treatment liquid and the second treatment liquid to the outside via the discharge flow path at the same time.

(6) According to a specific aspect, the treatment liquid production device according to any one of the descriptions (1) to (4) above may further include a discharge flow path connected to the first tank and the second tank; and at least one discharge pump provided to the discharge flow path. The at least one discharge pump may discharge the first treatment liquid in the first tank and the second treatment liquid in the second tank to the outside via the discharge flow path. The controller may cause the at least one discharge pump to discharge the first treatment liquid and the second treatment liquid individually to the outside via the discharge flow path.

(7) A treatment liquid production method, which is an aspect of the present disclosure, includes producing a first treatment liquid by applying a voltage between a pair of electrodes and generating plasma in a liquid during a first period; and producing a second treatment liquid by applying a voltage between a pair of electrodes and generating plasma in a liquid during a second period. The second period is longer than the first period. An initial oxidizing power of the first treatment liquid is higher than an initial oxidizing power of the second treatment liquid. A remaining oxidizing power of the second treatment liquid is higher than a remaining oxidizing power of the first treatment liquid.

(8) According to a specific aspect, in the treatment liquid production method according to the description (7) above, the first period may be substantially identical to a time at which, on a graph that indicates a relation between a plasma treatment time and the initial oxidizing power of the treatment liquid, the initial oxidizing power is a maximum value at a peak. The second period may be identical to a time at which, on a graph that indicates a relation between the plasma treatment time and the initial oxidizing power of the treatment liquid, the initial oxidizing power is a substantially saturated value.

With the treatment liquid production device and the treatment liquid production method according to the present disclosure, it is possible to produce a treatment liquid having a high oxidizing ability.

Referring to the accompanying drawings, more specific embodiments of the present disclosure will be described below. In the following description, the same or similar components are denoted by the same reference characters. Duplicate description thereof is omitted. The treatment liquid production device and the treatment liquid production method of the present disclosure are not limited to the embodiments exemplified in the following description.

First, referring to FIGS. 1 to 6, a configuration and an operation that are common to respective embodiments will be described. Treatment liquid production devices 10A to 10E according to respective embodiments are configured using a treatment liquid production unit 100 as a basic structure.

[Overall Configuration]

An overall configuration of the treatment liquid production unit 100 will be described with reference to FIG. 1.

FIG. 1 is an overall configuration diagram illustrating the treatment liquid production unit 100.

The treatment liquid production unit 100 produces a treatment liquid which is made to react with a treatment target. The treatment liquid contains active species. In the description of the present disclosure, an example in which a treatment liquid is produced by using tap water will be described. A treatment liquid produced by using water is referred to as "treatment water". For example, it is also possible to produce "treatment water" by using distilled water as a substitution for tap water.

The treatment liquid production unit 100 typically includes a plasma generating device 120, a treatment tank 109, a discharge flow path 115, and a discharge pump 116. The treatment liquid production unit 100 may further include a gas flow pump 105, a circulation flow path 300, and a circulation pump 108.

The plasma generating device 120 is configured to generate active species in a liquid by forming a gas bubble in the liquid and generating plasma in the gas bubble. Specifically, the plasma generating device 120 includes a first metal electrode 104, a second metal electrode 102, an insulating body 103, an opening section 125 (refer to FIG. 2), and a power supply 101.

On a wall in the treatment tank 109, the second metal electrode 102 and the first metal electrode 104, both of which penetrate the wall, are arranged, and ends of the respective electrodes are arranged inside the treatment tank 109. The first metal electrode 104 has a tubular shape, both ends of which are open, and, to an opening section at one end thereof, the gas flow pump 105 is connected as a gas supply device. The first metal electrode 104 may have a cylindrical shape.

The inside of the treatment tank 109 is filled with liquid 110 (tap water). For example, the treatment tank 109 has a capacity of approximately 250 mL (approximately 250 cm$^3$). The size of the treatment tank 109 is not limited to any specific size. For example, the treatment tank 109 may have a capacity in a range from 0.1 L to 1000 L.

The gas flow pump 105 supplies gas to the treatment tank 109 from the opening section 125 at the other end of the first metal electrode 104. The gas supplied from the outside of the treatment tank 109 includes air, He, Ar, $O_2$, or the like. The gas itself may be supplied from a gas supply source (not illustrated), or gas in the atmosphere in which the treatment tank 109 is arranged may be supplied directly.

The second metal electrode 102 has a cylindrical shape and is arranged in such a way that an end thereof is in contact with the liquid 110 in the treatment tank 109.

The power supply 101 applies a pulse voltage or an alternating voltage between the second metal electrode 102 and the first metal electrode 104.

The circulation pump 108 circulates the liquid 110. The circulation velocity of the liquid 110 may be set at an appropriate value based on a resolving power required by the treatment water and the capacity of the treatment tank 109. With the circulation pump 108, it is possible to uniformly treat the liquid 110. Even when the circulation pump 108 is not installed, it is possible to uniformly treat the liquid 110 because of natural convection or the like of the liquid 110.

The treatment tank 109 is connected to the discharge flow path 115. Treatment water produced in the treatment tank 109 is discharged to the outside via the discharge flow path 115. The discharge pump 116 is installed along the discharge flow path 115, and the discharge of a liquid is controlled according to whether or not a voltage is applied to the discharge pump 116.

The treatment liquid production unit 100 may include a liquid supplying flow path connected to the treatment tank 109. A liquid supplying pump may be installed along the liquid supplying flow path. With this configuration, it is possible to supply a new liquid to the treatment tank 109.

[Configuration of Electrodes]

Figure 2:
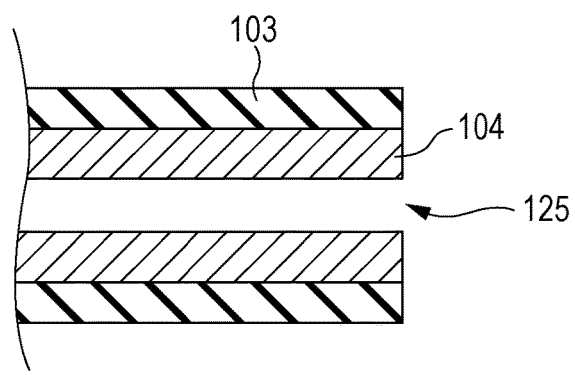
FIG. 2 is an enlarged cross-sectional view illustrating the vicinity of an opening section of a first metal electrode.

FIG. 2 is an enlarged sectional side view illustrating the vicinity of the opening section 125 of the first metal electrode 104. The first metal electrode 104 is an electrode that is made of a metal and has a cylindrical shape. The internal diameter and the external diameter of the first metal electrode 104 are 0.4 mm and 0.6 mm, respectively. The insulating body 103 is arranged around the outer peripheral surface of the first metal electrode 104. The insulating body 103 is arranged with the first metal electrode 104 without any space therebetween. Thus, the outer peripheral surface of the first metal electrode 104 is not in direct contact with the liquid 110. The insulating body 103 may be formed by, for example, directly depositing titanium oxide on the outer peripheral surface of the first metal electrode 104 by plasma spraying. The thickness of the insulating body 103 may be 0.1 mm. Titanium oxide does not have notable effects on the human body. Therefore, when a treatment liquid is used in daily life, it is desirable to use titanium oxide for the insulating body 103.

In the configuration described above, when gas is supplied continuously from the opening section 125 of the first metal electrode 104, a gas bubble 106 is formed in the liquid 110. At this time, the vicinity of the opening section 125 of the first metal electrode 104 is covered with gas in the gas bubble 106.

As illustrated in FIG. 2, the end face of the first metal electrode 104 on the side including the opening section 125 is not covered with the insulating body 103. However, by setting the quantity of gas supplied by the gas flow pump 105 at an appropriate value, it is possible to maintain a state in which the end face of the first metal electrode 104 is covered with the gas in the gas bubble 106.

As described previously, the insulating body 103 made of titanium oxide is arranged on the outer peripheral surface of the first metal electrode 104. Therefore, when an appropriate quantity of gas is supplied continuously, it is possible to maintain a state in which the surface of the first metal electrode 104 is not in direct contact with the liquid 110.

Figure 3:
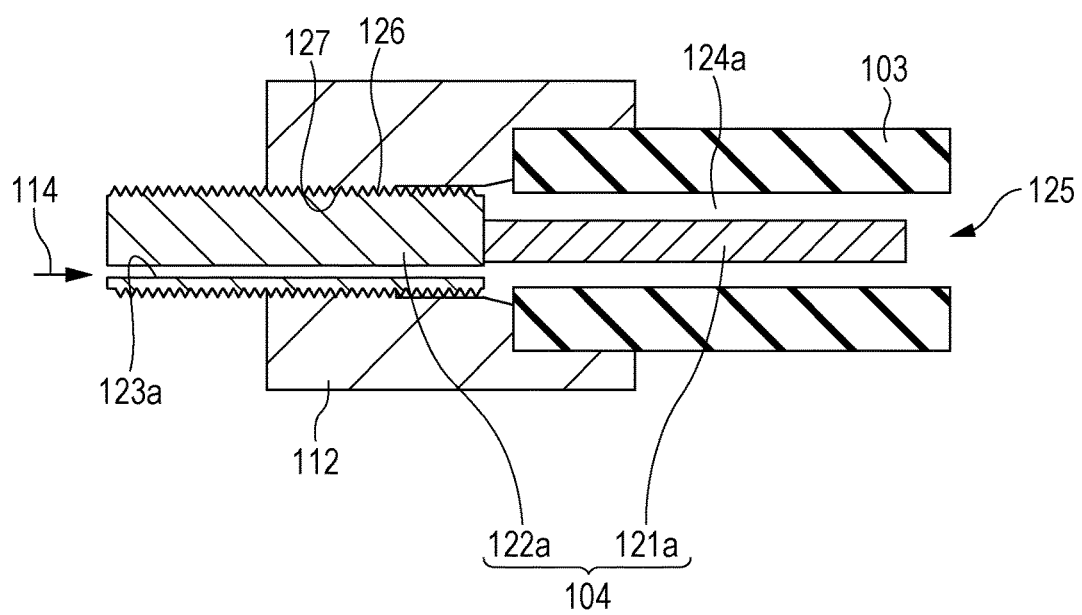
FIG. 3 is an exemplary cross-sectional view illustrating another configuration of the electrodes according to a first embodiment.

FIG. 3 is a cross-sectional view illustrating another configuration of the electrodes according to the embodiments.

The first metal electrode 104 has a metal electrode section 121a, which is arranged in the treatment tank 109, on one end portion thereof. The first metal electrode 104 has a metal screw section 122a on the other end portion thereof. The metal screw section 122a is fixed to a holding block 112 and connected to the power supply 101. The insulating body 103 is disposed in such a way as to form a space 124a with the metal electrode section 121a. The opening section 125, which forms the gas bubble 106 in the liquid 110, is disposed on the insulating body 103. Further, a screw section 126 is disposed on the outer periphery of the metal screw section 122a, and a through-hole 123a is disposed inside the metal screw section 122a.

In the first metal electrode 104, the metal electrode section 121a and the metal screw section 122a may have different sizes and be formed with different materials. In the embodiments, as an example, the metal electrode section 121a has a diameter of 0.95 mm and is made of tungsten. The metal screw section 122a has a diameter of 3 mm and is made of iron. The metal electrode section 121a may have a diameter large enough to generate a plasma, and the diameter may be 2 mm or less. The material of the metal electrode section 121a is not limited to tungsten. For the material of the metal electrode section 121a, another plasma-resistant metal material may be used. Copper, aluminum, iron, or an alloy thereof may be used. Moreover, on a portion of the surface of the metal electrode section 121a, yttrium oxide mixed with a conductive material may be deposited by thermal spraying. For the conductive material, for example, yttrium metal may be used, and mixing the conductive material makes it possible to provide a conductivity of 1 to 30 Ωcm. Thermal spraying of yttrium oxide may have an advantageous effect of extending the life of an electrode.

On the other hand, the diameter of the metal screw section 122a is not limited to 3 mm. It is sufficient for the diameter of the metal screw section 122a to be larger than the diameter of the metal electrode section 121a. The material of the metal screw section 122a may be a metal material that can be processed easily, and, for example, a material generally used for a screw may be used. Specifically, the material of the metal screw section 122a may be copper, zinc, aluminum, tin, brass, or the like. The first metal electrode 104, for example, may be formed by combining the metal electrode section 121a and the metal screw section 122a into a single unit by pressing the metal electrode section 121a into the metal screw section 122a. In this way, a metal material having a high plasma resistance may be used for the metal electrode section 121a, and a metal material that can be processed easily may be used for the metal screw section 122a. With this configuration, it is possible to provide a metal electrode having plasma resistance, a low manufacturing cost, and stable characteristics.

To the metal screw section 122a, the through-hole 123a which leads to the gas flow pump 105 is disposed. The through-hole 123a is linked to the space 124a, and gas 114 from the gas flow pump 105 is supplied to the space 124a via the through-hole 123a. The metal electrode section 121a is covered with the gas 114 supplied via the through-hole 123a. In a case of a single through-hole 123a, as illustrated in FIG. 3, the through-hole 123a of the metal screw section 122a may be disposed on the lower side so that the gas 114 is supplied from the lower side of the metal electrode section 121a. With this configuration, it becomes easier for the metal electrode section 121a to be covered with the gas 114. Further, disposing two or more through-holes 123a is advantageous for suppressing a pressure drop in the through-holes 123a. The through-hole 123a has a diameter of, for example, 0.3 mm.

On the outer periphery of the metal screw section 122a, the screw section 126 may be disposed. For example, the screw section 126 on the outer periphery of the metal screw section 122a may be a male screw. In this case, disposing a screw section 127 which is a female screw to the holding block 112 makes it possible to fix the first metal electrode 104 to the holding block 112 by screwing the screw section 126 and the screw section 127 together. By rotating the metal screw section 122a, it is possible to accurately adjust the position of the end face of the metal electrode section 121a with respect to the opening section 125 disposed on the insulating body 103. Further, it is also possible to connect and fix the first metal electrode 104 to the power supply 101 by screwing them together with the screw sections 126 and 127. With this configuration, contact resistance becomes stable, and it becomes possible to provide stable characteristics. It is also possible to securely connect the first metal electrode 104 to the gas flow pump 105.

Around the metal electrode section 121a, for example, the insulating body 103 with an internal diameter of 1 mm is arranged. Between the metal electrode section 121a and the insulating body 103, the space 124a is formed. To the space 124a, the gas 114 is continuously supplied from the gas flow pump 105 via the through-hole 123a. The metal electrode section 121a is covered with the gas 114. Therefore, although the outer periphery of the metal electrode section 121a is exposed, the metal electrode section 121a is not in direct contact with the liquid 110 in the treatment tank 109. To the insulating body 103, the opening section 125 is formed. The gas 114 is discharged into the liquid 110 in the treatment tank 109 via the opening section 125. The discharged gas 114 forms the gas bubble 106 in the liquid 110. The size of the gas bubble 106 depends on the opening section 125. The material of the insulating body 103 is not limited to alumina ceramic, and, for example, magnesia, quartz, or yttrium oxide may be used.

As illustrated in FIG. 3, the opening section 125 of the insulating body 103 is formed on the end face of the insulating body 103. However, the opening section 125 may be formed on a side face of the insulating body 103. A plurality of opening sections 125 may be formed on the insulating body 103. The opening section 125 has a diameter of, for example, 1 mm.

The material of the second metal electrode 102 is not limited to a specific material. A wide variety of conductive metal materials may be used. For example, copper, aluminum, iron, or the like may be used.

With the configuration described above, it is possible to continue supplying the gas 114 to the space 124a. With this configuration, the gas bubble 106 is formed in the liquid 110. The gas bubble 106 becomes a gas bubble having a columnar shape and a size large enough for the opening section 125 of the insulating body 103 to be covered with gasses therein. As described above, the opening section 125 has a function to form the gas bubble 106 in the liquid 110. Setting the quantity of gas supplied by the gas flow pump 105 to an appropriate value makes it possible to maintain a state in which the metal electrode section 121a is covered with the gas 114.

In the description of the present disclosure, the description "the metal electrode section (or the surface of the metal electrode section) is not in direct contact with the liquid (treatment water)" means that the surface of the metal electrode section does not come into contact with a liquid as a large mass in a reaction tank. Thus, for example, when the gas bubble is formed while the surface of the metal electrode section is wetted by the liquid, there is a case in which the surface of the metal electrode section is covered with the gas in the gas bubble while the surface of the metal electrode section is kept wetted by the liquid (that is, strictly speaking, in a state in which the surface of the metal electrode section is in contact with the liquid). It is assumed that this state includes the state in which "the metal electrode section is not in direct contact with the liquid".

[Basic Operation]

Next, a basic operation of the treatment liquid production unit 100 will be described.

First, to produce treatment water, tap water (liquid) 110 is supplied to the treatment tank 109. Next, by the gas flow pump 105, gas is supplied to the tap water 110 from the opening section 125 on an end of the first metal electrode 104 that is positioned in the treatment tank 109. The flow rate of the gas is, for example, 0.5 to 2.0 L/min. In the tap water 110, the gas bubble 106 which has a columnar shape and covers the opening section 125 with the gas therein is formed. The gas bubble 106 becomes a single large gas bubble which expands from the opening section 125 to a certain size (20 mm or more in the illustrated embodiment) without a break. In other words, by the gas supply, the surrounding area of the opening section 125 is positioned in the gas bubble 106 and becomes covered by the gas in the gas bubble 106. In the liquid, a gas-liquid interface, which defines the gas bubble 106, is "not closed". The gas bubble 106 is in contact with the insulating body 103 around the opening section 125. By forming the gas bubble 106, the surface of the first metal electrode 104 can be separated from the tap water 110 by the gas bubble 106 and the insulating body 103. That is, when the gas bubble 106 is formed, for example, in a case of the first metal electrode 104 being embodied as illustrated in FIG. 2, the inner surface (inner peripheral surface) of the first metal electrode 104 is covered with the supplied gas and is not in direct contact with the tap water 110. In a case of the first metal electrode 104 being embodied as illustrated in FIG. 3, the outer surface (outer peripheral surface) of the first metal electrode 104 is covered with the supplied gas and is not in direct contact with the tap water 110.

During a period in which a voltage is applied between the first metal electrode 104 and the second metal electrode 102, the surrounding area of the opening section 125 is continuously positioned in the gas bubble 106. That is, the surrounding area of the opening section 125 is continuously covered with the gas in the gas bubble 106. However, when the quantity of gas supply (flow rate) is low, there may be a case in which, even if the gas is supplied continuously, the surrounding area of the opening section 125 is not positioned in the gas bubble 106, and the first metal electrode 104 is in direct contact with the tap water 110. It is possible to confirm the existence or nonexistence of such contact by taking pictures with a high-speed camera. For example, it is possible to confirm the existence or nonexistence of contact by taking pictures of the surrounding area of the first metal electrode 104 every 0.1 to 0.5 ms during a period in which the gas bubble is supplied.

The surrounding area of the first metal electrode 104 may be observed by taking pictures with a high-sensitivity camera while supplying the gas continuously for 1 to 30 seconds. By calculating an electrode coverage ratio with the following formula, it is possible to obtain a contact frequency between the first metal electrode 104 and the liquid. Whether or not the exposed surface of the conductor of the first metal electrode is positioned in the gas bubble may be determined visually by viewing the captured images. In the present disclosure, it is desirably to supply the gas so that the electrode coverage ratio has a value of 90% or more. Furthermore, it is more desirably to supply the gas so that the electrode coverage ratio has a value of 94% or more.

Electrode coverage ratio (%)=[(number of images (pictures) in which the exposed surface of the conductor of the first metal electrode is positioned in the gas bubble)/(total number of images (pictures) captured)]×100

After reaching a state in which the first metal electrode 104 is covered with the gas bubble 106 and is not in direct contact with the tap water 110, a voltage is applied between the first metal electrode 104 and the second metal electrode 102. Specifically, while the second metal electrode 102 is grounded, a pulse voltage is applied to the first metal electrode 104. For example, a pulse voltage with a peak voltage of 4 kV, a pulse width of 1 μs, and a frequency of 30 kHz may be applied.

The supplied electric power is, for example, 200 W. By applying a voltage between the first metal electrode 104 and the second metal electrode 102, plasma 107 is generated in the vicinity of the first metal electrode 104. The plasma 107 spreads throughout the gas bubble 106. In particular, highly-concentrated plasma 107 is formed in the vicinity of the first metal electrode 104. It has been found that the plasma 107 is also formed inside the first metal electrode 104 (an inner peripheral portion of the first metal electrode 104 having a tubular shape), and not only the end but also the whole electrode is effectively utilized.

The distance between the first metal electrode 104 and the second metal electrode 102 is not limited to any specific value. For example, the distance between the electrodes does not have to be limited to a value in a range from 1 to 50 mm as disclosed in Japanese Unexamined Patent Application Publication No. 2009-255027. By configuring the electrodes according to the present disclosure, it is possible to generate the plasma 107, even if the electrodes are distanced from each other by, for example, more than 50 mm.

Furthermore, the first metal electrode 104 and the second metal electrode 102 do not have to face each other. There is no constraint to the position at which the second metal electrode 102 is arranged as long as, in the treatment tank 109, at least a portion of the second metal electrode 102 is in contact with the liquid 110. This is because the second metal electrode 102 being in contact with the liquid 110 causes the whole liquid to function as an electrode. It is thought that when viewed from the first metal electrode 104 the whole surface of the liquid 110, which is in contact with the gas bubble 106, functions as an electrode.

The frequency of the pulse voltage is not limited to any specific value. For example, it is possible to generate the plasma 107 sufficiently by applying a pulse voltage with a frequency of 1 Hz to 30 kHz. On the other hand, the voltage is determined not only by the capacity of a power supply, but also by the impedance of a load. There is also an advantage in that, in applying a pulse voltage, applying a positive pulse voltage and a negative pulse voltage alternately, a so-called bipolar pulse voltage, extends the life of the electrodes. In the treatment liquid production unit 100, for example, a power supply having a capacity capable of outputting a voltage of 6 kV when there is no load is used. As described above, the power supply is capable of applying a voltage of 4 kV when a load including the electrodes is connected. In this way, it is possible to form the plasma 107 with a low voltage loss.

In the above description, although the internal diameter and the external diameter of the first metal electrode 104 are set at 0.4 mm and 0.6 mm, respectively, the internal diameter and the external diameter are not limited to these values. For example, it is possible to form the plasma 107 even when the internal diameter and the external diameter are set at 0.07 to 2.0 mm and 0.1 to 3.0 mm, respectively.

In the treatment liquid production unit 100, the length of a portion of the first metal electrode 104 that is positioned inside the treatment tank 109 is approximately 10 mm. However, without being limited to the value, the length of the portion of the first metal electrode 104 that is positioned inside the treatment tank 109 may have a value of, for example, 0.1 to 25 mm. If the length of the portion of the first metal electrode 104 that is positioned inside the treatment tank 109 is short, the gas bubble 106 formed in the vicinity of the opening section 125 cannot spread in directions toward the wall of the treatment tank 109. That is because the gas bubble 106 comes in contact with the wall. In consequence, the area of the gas-liquid interface decreases, and the amount of plasma 107 tends to decrease. However, the plasma 107 is generated for as long as the first metal electrode 104 is positioned inside the treatment tank 109. The treatment liquid production unit 100 has a large tolerance to electrode size.

[Basic Effect (OH Radical Generation)]

Figure 4:
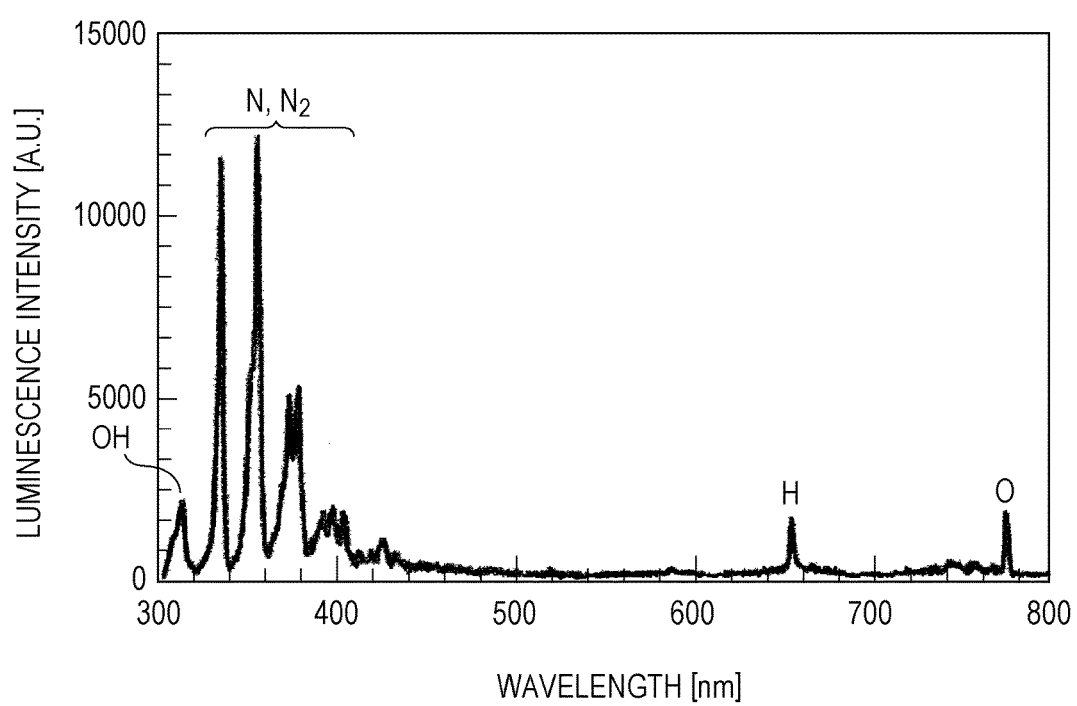
FIG. 4 is a graph illustrating a result from measuring a luminescence characteristic of plasma by using a spectrometer.

FIG. 4 is a graph illustrating a result from measuring a luminescence characteristic of plasma by using a spectrometer. In FIG. 4, the horizontal axis represents wavelength (nm), and the vertical axis represents luminescence intensity (a.u.). In the measurement, treatment water 110 produced from tap water was used. In the measurement, water temperature was 26.5° C. and electric conductivity was 20.3 mS/m.

As illustrated in FIG. 4, luminescence caused by OH radicals produced by water decomposition is confirmed. Further, luminescence of $N_2$, N, H, and O is also confirmed. The luminescence of $N_2$ and N is caused by air being supplied to the tap water 110 as the gas. In this way, plasma generated by the treatment liquid production unit 100 has a characteristic of plasma generated in the water and a characteristic of plasma generated in the air.

[Basic Characteristic (Oxidizing Power)]

(Initial Oxidizing Power)

Figure 5:
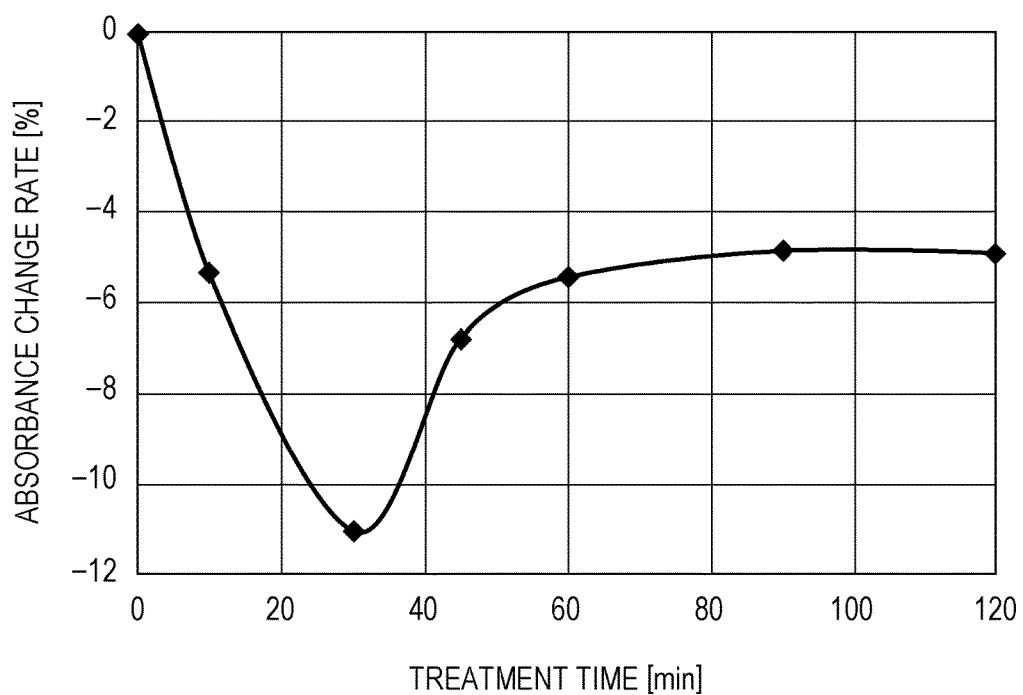
FIG. 5 is a graph illustrating a relation between treatment time of the treatment liquid production unit and the initial oxidizing power of treatment water.

FIG. 5 is a graph illustrating a relation between treatment time and oxidizing power (initial oxidizing power) that treatment water has immediately after plasma treatment, in the treatment liquid production unit 100. In FIG. 5, the horizontal axis represents treatment time, and the vertical axis represents an absorbance change rate. The treatment time indicates the time from start to finish of plasma treatment of an untreated liquid.

Oxidizing power of treatment water obtained by plasma treatment changes as time passes after the plasma treatment. In the description of the present disclosure, "initial oxidizing power" means oxidizing power of treatment water in a relatively short time after the plasma treatment has finished. Specifically, the initial oxidizing power means oxidizing power in 30 to 60 seconds after the plasma treatment has finished.

In order to measure the oxidizing power of treatment water, an indigo carmine aqueous solution was used. An indigo carmine aqueous solution is a water-soluble organic substance and is widely used as a model of polluted water treatment.

As described above, OH radicals (active species) are generated in tap water in the treatment tank 109. With this process, treatment water is obtained. This treatment water is made to react with the indigo carmine aqueous solution. The OH radicals in the treatment water react with the indigo carmine aqueous solution to break bonds in molecules. With this reaction, the indigo carmine molecules are broken down. An oxidizing potential of OH radicals is, as is generally known, 2.81 eV. The oxidizing potential of OH radicals is larger than the oxidizing potentials of ozone, hydrogen peroxide, and chlorine. Thus, OH radicals are capable of breaking down not only indigo carmine but also many types of organic substances.

The degree of breakdown of indigo carmine molecules can be evaluated by the absorbance of an aqueous solution thereof. It is generally known that, when indigo carmine molecules are broken down, a blue color of the indigo carmine aqueous solution disappears, and, when the indigo carmine molecules are completely broken down, the indigo carmine aqueous solution becomes transparent (slightly yellow-tinted). That is because the absorbing wavelength of double bonds of carbon ($C=C$), which are included in the indigo carmine molecules, is 608.2 nm. The breakdown of the indigo carmine molecules causes cleavage of bonds in $C=C$, and absorption of light with a wavelength of 608.2 nm disappears.

As described above, it is possible to regard the degree of breakdown of indigo carmine molecules as an index of oxidizing power. Thus, the oxidizing power was evaluated by measuring the absorbance of light with a wavelength of 610 nm by using an ultraviolet-visible spectrophotometer. The oxidizing power may be evaluated by measuring the absorbance of light with a wavelength of 608.2 nm. In the description of the present disclosure, the "oxidizing power" means how much the absorbance of an indigo carmine aqueous solution changes by treatment water. That is, the oxidizing power is represented by the absorbance change rate which is calculated as dividing an amount of change in the absorbance of the indigo carmine aqueous solution between before and after mixing treatment water by the absorbance of the indigo carmine aqueous solution before mixing treatment water.

Specifically, 20 μL of a 1000 ppm indigo carmine aqueous solution and 1.98 mL of treatment water were prepared. The indigo carmine aqueous solution and the treatment water were mixed and stirred. When 30 seconds had passed after mixing, the absorbance of light with a wavelength of 610 nm was measured by using an ultraviolet-visible spectrophotometer. A result obtained in this way is illustrated in FIG. 5.

Because treatment water causes a decoloration reaction, the absorbance change rate takes negative values. A higher absolute value of the absorbance change rate means a higher oxidizing power.

As illustrated in FIG. 5, as the treatment time becomes longer, the absolute value of the absorbance change rate drastically increases. In other words, it is indicated that the initial oxidizing power of the treatment water drastically rises. As the treatment time becomes further longer, the initial oxidizing power takes a peak value, and, thereafter, the initial oxidizing power gradually falls. Specifically, the initial oxidizing power takes a maximum value at a treatment time of 30 minutes, and, when the treatment time surpasses 60 minutes, the initial oxidizing power becomes approximately constant.

It is thought that dominant active species in the treatment water with respect to each treatment time differ from one another.

(Remaining Oxidizing Power)

Figure 6:
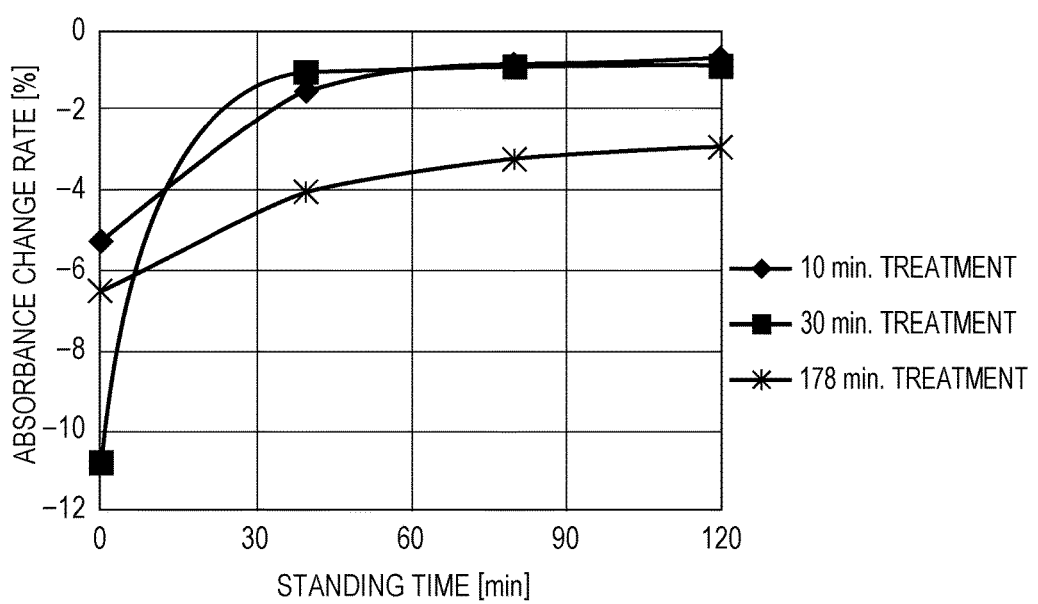
FIG. 6 is a graph illustrating a temporal change in the remaining oxidizing power with respect to standing time.

FIG. 6 illustrates how the oxidizing power of treatment water changes with respect to standing time. The evaluation of the oxidizing power was carried out by the same method as the evaluation of the initial oxidizing power. That is, how much the absorbance of an indigo carmine aqueous solution changes by treatment water, that is, the above-described absorbance change rate was evaluated.

In the description of the present disclosure, the "remaining oxidizing power" means the oxidizing power of treatment water after the treatment water having been left standing for a long time since plasma treatment finished. That is, the remaining oxidizing power means the oxidizing power remaining in treatment water after the treatment water having been left standing for a long time. In the definition, the "long time" means, for example, 120 minutes.

The result illustrated in FIG. 6 was measured in the following way. First, several types of treatment water with plasma treatment times differing from one another were prepared. Specifically, three types of treatment water with plasma treatment times differing from one another, namely 10, 30, and 178 minutes, respectively, were prepared. With respect to each type of treatment water, treatment liquids were sampled when 40, 80, and 120 minutes had passed since the plasma treatment finished. Immediately after the sampling of the treatment liquids, 1.98 ml of the sampled treatment liquid was mixed with 20 µL of an indigo carmine aqueous solution, and the absorbance change rate in 30 seconds was measured.

As illustrated in FIG. 6, the oxidizing power of treatment water with a short plasma treatment time becomes low when being left standing for a long time. In particular, the initial oxidizing power of treatment water with a treatment time of 30 minutes is high but the oxidizing power thereof decreases significantly when being left standing for a long time. On the other hand, although treatment water with a long plasma treatment time has lower initial oxidizing power than treatment water with a plasma treatment time of 30 minutes, the decrease in the oxidizing power thereof is small even when being left standing for a long time. As the result illustrates, by adjusting the plasma treatment time, it becomes possible to produce selectively treatment water having a superiority in initial oxidizing power and treatment water having a superiority in the remaining oxidizing power.

First Embodiment

Figure 7:
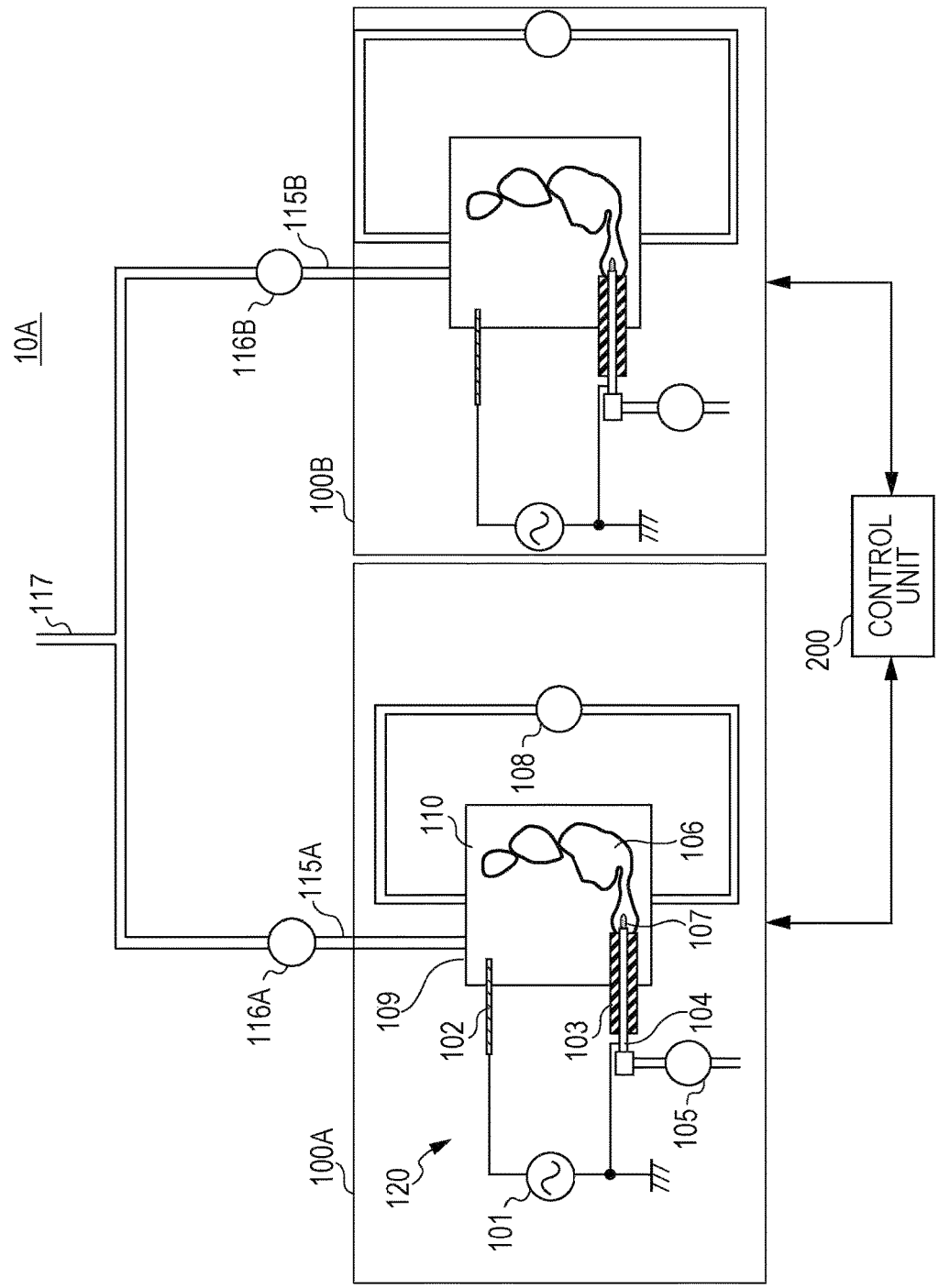
FIG. 7 is an exemplary overall configuration diagram illustrating a treatment liquid production device according to the first embodiment.

Referring to FIG. 7, a treatment liquid production device 10A according to a first embodiment will be described.

FIG. 7 is an overall configuration diagram illustrating the treatment liquid production device 10A according to the first embodiment. The treatment liquid production device 10A includes a first treatment liquid production unit 100A, a second treatment liquid production unit 100B, and a control unit 200 (it is also called controller). The first treatment liquid production unit 100A and the second treatment liquid production unit 100B have the same structure as the above-described treatment liquid production unit 100.

To the first treatment liquid production unit 100A, a discharge flow path 115A is connected. A discharge pump 116A is installed along the discharge flow path 115A. To the second treatment liquid production unit 100B, a discharge flow path 115B is connected. A discharge pump 116B is installed along the discharge flow path 115B. The discharge flow path 115A and the discharge flow path 115B are connected to a discharge flow path 117.

The first treatment liquid production unit 100A generates plasma during a first period to produce first treatment water. The first period is set based on the graph illustrated in FIG. 5, which was described in relation to the treatment liquid production unit 100. As described earlier, the absorbance change rate takes a minimum value for a relatively short treatment time. It is desirable that the first period is set at a period substantially the same as the treatment time for which the absorbance change rate takes the minimum value. For example, it is desirable that the first period is set within the range of ±20% centering the treatment time for which the absorbance change rate takes the minimum value. In particular, for example, when treatment water has a characteristic as illustrated in FIG. 5, it is desirable that the first period is set within the range of 24 to 36 minutes. Setting the first period in such a manner makes it possible to obtain first treatment water having a high initial oxidizing power by the first treatment liquid production unit 100A. The first period may be set at a period which is in a range where the graph exhibits a downward convex curve and the absorbance change rate takes a smaller value than a substantially saturated value. For example, when treatment water has a characteristic as illustrated in FIG. 5, the absorbance change rate is saturated at about −5% for sufficiently long treatment time. Therefore, the first period may be set at, for example, 10 to 50 minutes, which is a period at which the absorbance change rate takes a value less than the saturation value.

The second treatment liquid production unit 100B produces second treatment water during a second period, which is longer than the first period. The second period is also set based on the graph illustrated in FIG. 5 described above. As described earlier, the absorbance change rate is saturated for sufficiently long treatment time. The second period is set at a period in which the absorbance change rate is substantially saturated and takes almost a constant value. For example, the second period is set at a period in which the absorbance change rate is within the range of ±10% of a saturated value. For example, when treatment water has a characteristic as illustrated in FIG. 5, the second period may be set at 60 to 100 minutes. As described above, carrying out plasma treatment for a sufficient period to saturate the absorbance change rate makes it possible to obtain treatment water having a high remaining oxidizing power. Therefore, setting the second period in such a manner makes it possible to obtain second treatment water having a high remaining oxidizing power by the second treatment liquid production unit 100B.

The control unit 200 controls the whole of the treatment liquid production device 10A. The control unit 200 controls respective periods to produce treatment water in the first treatment liquid production unit 100A and the second treatment liquid production unit 100B. Specifically, the control unit 200 controls the first treatment liquid production unit 100A so that first treatment liquid is produced in the first period. The control unit 200 also controls the second treatment liquid production unit 100B so that second treatment liquid is produced in the second period. The first treatment liquid production unit 100A thereby produces the first treatment water. The second treatment liquid production unit 100B produces the second treatment water. The initial oxidizing power of the first treatment water is higher than the initial oxidizing power of the second treatment water, and the remaining oxidizing power of the second treatment water is higher than the remaining oxidizing power of the first treatment water.

The control unit 200 differentiates timings at which voltages are applied between the first metal electrodes 104 and the second metal electrodes 102 in respective treatment liquid production units. For example, the control unit 200 may carry out control so that the first treatment liquid production unit 100A and the second treatment liquid production unit 100B finish producing treatment water at the same time. In that case, operation of the second treatment liquid production unit 100B is started first. After 60 minutes have passed since the start of operation of the second treatment liquid production unit 100B, operation of the first treatment liquid production unit 100A is started. After another 30 minutes have passed since the start of operation of the first treatment liquid production unit 100A, operation of the first treatment liquid production unit 100A and the second treatment liquid production unit 100B are stopped at the same time. With this method, it is possible to produce the first treatment water and the second treatment water at the same timing. Generation of treatment water may be started at the same time as another method. In that case, the first treatment water is produced first.

The treatment water produced by the first treatment liquid production unit 100A is jetted to the outside by the discharge pump 116A through the discharge flow path 115A and the discharge flow path 117. The treatment water produced by the second treatment liquid production unit 100B is jetted to the outside by the discharge pump 116B through the discharge flow path 115B and the discharge flow path 117. The jetted treatment water is made to be in contact with a treatment target. The treatment target may be a liquid containing a harmful substance, such as a fungus, or a deposit of fungus itself.

An example of control of the discharge pumps 116A and 116B will be described below.

The control unit 200 may control the discharge pumps 116A and 116B in such a way that mixed water in which the first treatment water is mixed with the second treatment water is discharged from the discharge flow path 117. With this configuration, it is possible to obtain mixed water having a high initial oxidizing power and a high remaining oxidizing power.

Alternatively, the control unit 200 may control the discharge pumps 116A and 116B in such a way that, after the first treatment water is discharged from the discharge flow path 117, the second treatment water is discharged from the discharge flow path 117. With this configuration, it is possible to make treatment water having a high initial oxidizing power and treatment water having a high remaining oxidizing power react with a target in order.

It is possible to omit the discharge flow path 117. In this case, the first treatment water is discharged from the discharge flow path 115A, and the second treatment water is discharged from the discharge flow path 115B.

In substitution for installing the discharge pumps 116A and 116B, a discharge pump may be installed along the discharge flow path 117, and on-off valves may be installed along the discharge flow paths 115A and 115B. With this configuration, it is possible to carry out a similar operation by a single discharge pump.

It is also possible to prescribe the operation of the control unit 200 described above as a treatment liquid production method.

Figure 8:
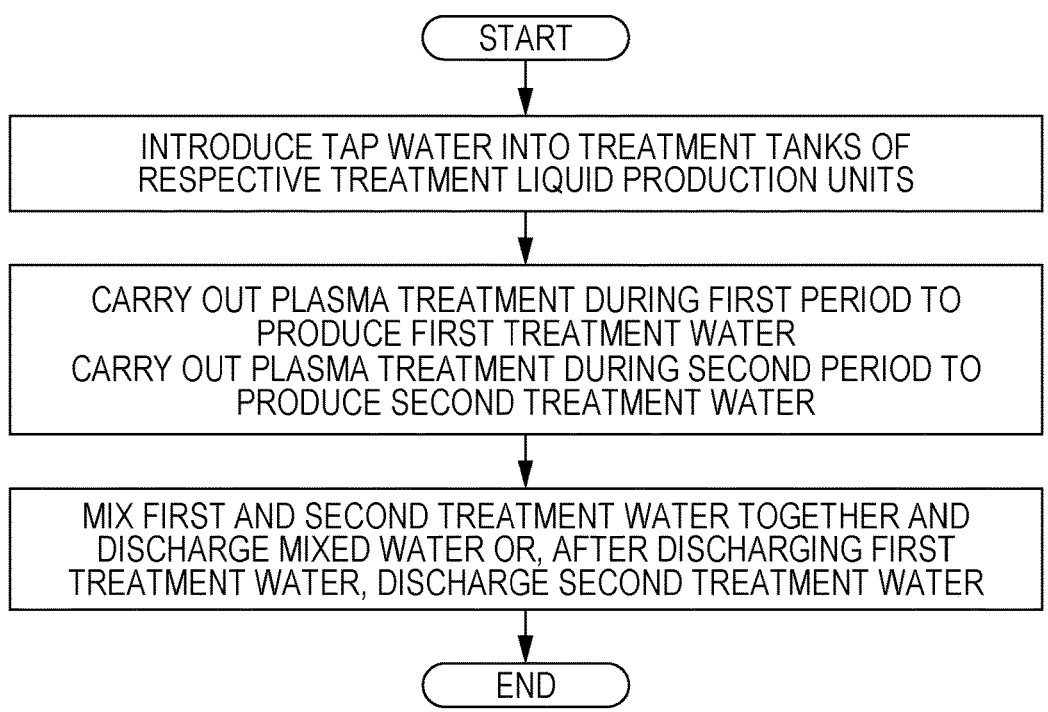
FIG. 8 is an exemplary flowchart illustrating a treatment liquid production method according to the first embodiment.

FIG. 8 illustrates an example of a process flow of a treatment liquid production method according to the first embodiment.

First, tap water is introduced into respective treatment tanks 109 of the treatment liquid production unit 100A and the treatment liquid production unit 100B.

Next, during the second period, the second treatment liquid is produced by forming a gas bubble in the tap water in the treatment tank 109 of the treatment liquid production unit 100B and generating plasma in the gas bubble. During the first period, which is shorter than the second period, the first treatment liquid is produced by forming a gas bubble in the tap water in the treatment tank 109 of the treatment liquid production unit 100A and generating plasma in the gas bubble. The timings at which the operations of producing treatment water finish may be set at the same moment in both periods. Alternatively, the timings at which the operations of producing treatment water start may be set at the same moment in both periods. Next, a mixed liquid may be produced by mixing the first treatment liquid and the second treatment liquid, and the mixed liquid may be discharged from the discharge flow path and made to be in contact with a target. Alternatively, the first treatment liquid may be discharged and made to be in contact with the target, and, then, the second treatment liquid may be discharged and made to be in contact with the target.

With the first embodiment, it is possible to make treatment water having a high oxidizing power react with a target on a long-term basis. By the oxidizing power of the treatment water, for example, smell components, funguses, and harmful components to human body are decomposed. In this manner, it is possible to achieve advantageous effects in deodorization, pasteurization, and sterilization.

In the first embodiment, a first plasma generating device is exemplified by a plasma generating device 120 included in the first treatment liquid production unit 100A. A second plasma generating device is exemplified by a plasma generating device 120 included in the second treatment liquid production unit 100B. A first tank is exemplified by a first treatment tank 109 included in the first treatment liquid production unit 100A. A second tank is exemplified by a second treatment tank 109 included in the second treatment liquid production unit 100B. A discharge flow path is exemplified by the discharge flow paths 115A, 115B, and 117. At least one discharge pump is exemplified by the discharge pumps 116A and 116B.

Variation of First Embodiment

Figure 9:
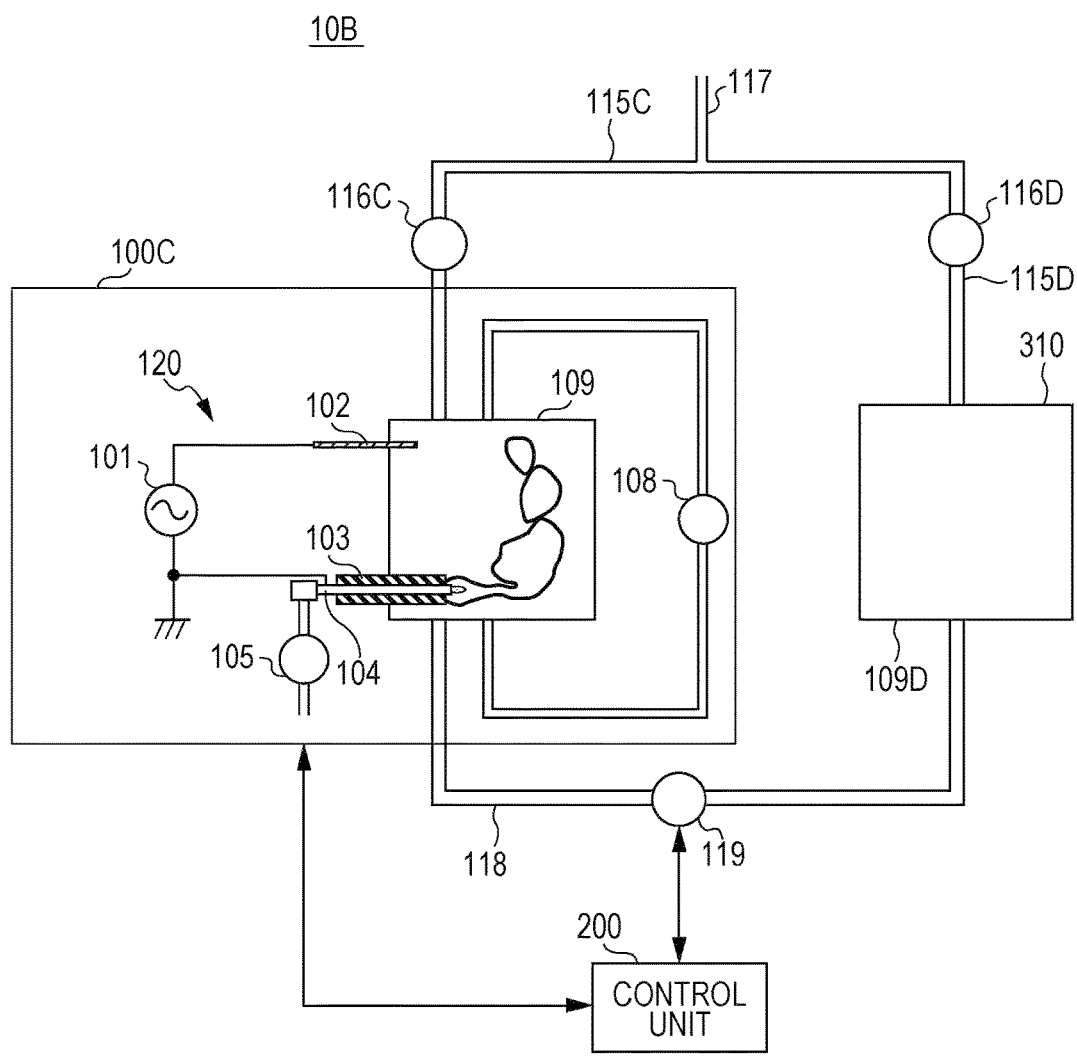
FIG. 9 is an exemplary overall configuration diagram illustrating a treatment liquid production device according to a variation of the first embodiment.

In the first embodiment, two treatment liquid production units are used. However, it is possible to configure a treatment liquid production device with a treatment liquid production unit. Referring to FIG. 9, a treatment liquid production device 10B according to a variation of the first embodiment will be described. Description of the same components as the first embodiment will be omitted.

FIG. 9 is an overall configuration diagram illustrating the treatment liquid production device 10B according to the variation of the first embodiment. The treatment liquid production device 10B includes a treatment liquid production unit 100C, a water storage tank 310, and a control unit 200. The treatment liquid production unit 100C has the same structure as the above-described treatment liquid production unit 100. The water storage tank 310 is connected to a treatment tank 109 of the treatment liquid production unit 100C by a connection flow path 118. A connection pump 119 is installed along the connection flow path 118. By the connection pump 119, treatment water in the treatment tank 109 of the treatment liquid production unit 100C is transmitted to the water storage tank 310.

To the treatment liquid production unit 100C, a discharge flow path 115C is connected. A discharge pump 116C is installed along the discharge flow path 115C. To the water storage tank 310, a discharge flow path 115D is connected. A discharge pump 116D is installed along the discharge flow path 115D. The discharge flow path 115C and the discharge flow path 115D are connected to a discharge flow path 117.

The control unit 200 controls the whole of the treatment liquid production device 10B. Specifically, the control unit 200 controls the treatment liquid production unit 100C to produce treatment water. The control unit 200 also controls the connection pump 119 to transfer treatment water in the treatment tank 109 of the treatment liquid production unit 100C to the water storage tank 310. Further, the control unit 200 controls the discharge pumps 116C and 116D to discharge the produced treatment water to the outside.

Next, an operation of the treatment liquid production device 10B will be described. A "first period" and a "second period" are the same as the first period and the second period described in the first embodiment, respectively.

First, tap water is introduced into the treatment tank 109 of the treatment liquid production unit 100C. Then, during the second period, second treatment water is produced by generating plasma in the tap water in the treatment tank 109 of the treatment liquid production unit 100C. Then, by making the connection pump 119 work, the treatment water produced in the treatment tank 109 is transferred to the water storage tank 310. With this operation, the second treatment water is accumulated in the water storage tank 310. On the other hand, the treatment tank 109 becomes empty.

Next, new tap water is introduced into the treatment tank 109 of the treatment liquid production unit 100C. Then, during the first period, first treatment water is produced by generating plasma in the tap water in the treatment tank 109 of the treatment liquid production unit 100C. With this operation, the treatment tank 109 becomes accumulated with the first treatment water, and the water storage tank 310 becomes accumulated with the second treatment water. Operations afterward are the same as the first embodiment. That is, mixed water may be produced by mixing the first treatment water and the second treatment water, and the mixed water may be discharged from the discharge flow path 117 and made to be in contact with a target. Alternatively, the first treatment water may be discharged and made to be in contact with the target, and, then, the second treatment water may be discharged and made to be in contact with the target.

With the variation of the first embodiment, it is possible to produce treatment water having a superiority in the initial oxidizing power and treatment water having a superiority in the remaining oxidizing power by a single treatment liquid production unit.

In the variation of the first embodiment, a plasma generating device is exemplified by a plasma generating device 120 included in the treatment liquid production unit 100C. A first tank is exemplified by the treatment tank 109 included in the treatment liquid production unit 100C. A second tank is exemplified by the water storage tank 310. A discharge flow path is exemplified by the discharge flow paths 115C, 115D, and 117. At least one discharge pump is exemplified by the discharge pumps 116C and 116D.

Second Embodiment

Figure 10:
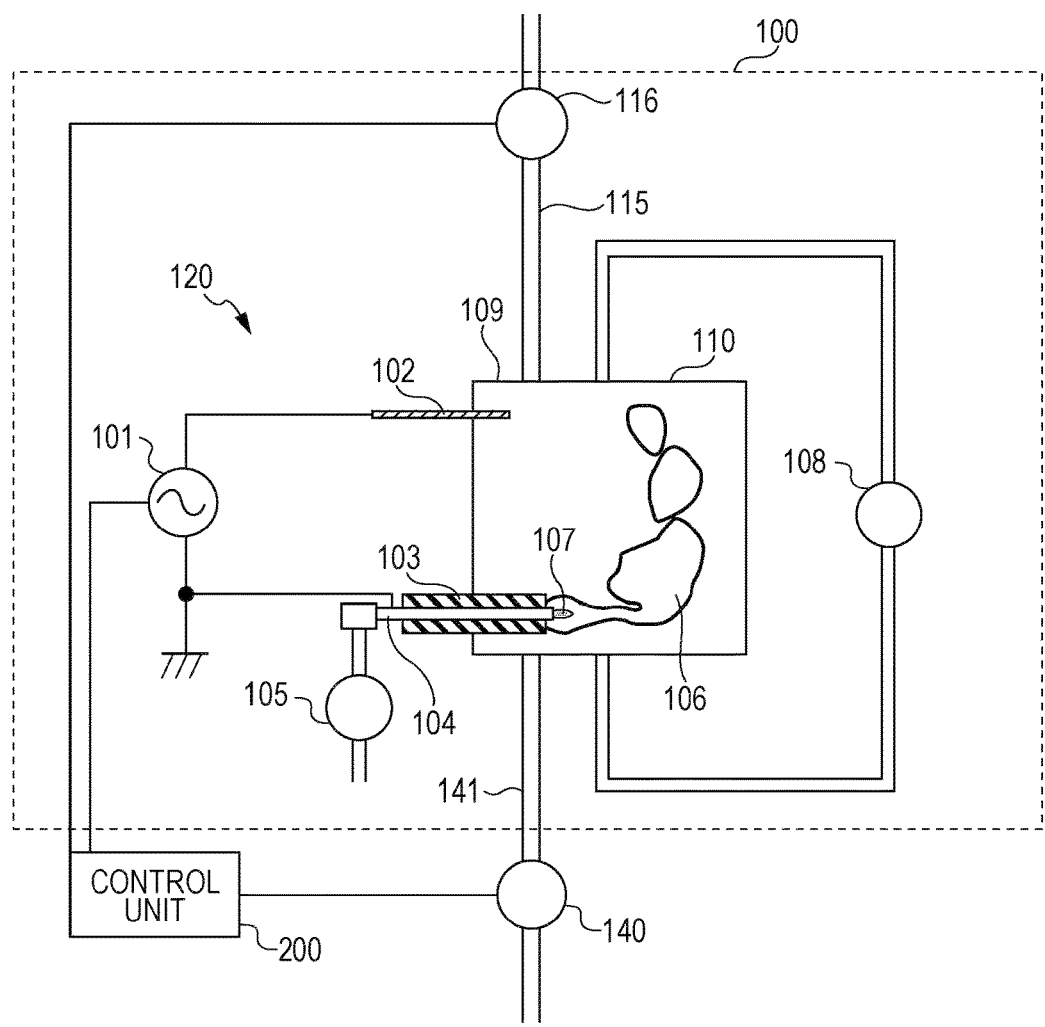
FIG. 10 is an exemplary overall configuration diagram illustrating a treatment liquid production device according a second embodiment.

Referring to FIG. 10, a treatment liquid production device 10C according to a second embodiment will be described.

FIG. 10 is an overall configuration diagram illustrating the treatment liquid production device 10C according to the second embodiment. The treatment liquid production device 10C includes a treatment liquid production unit 100, a control unit 200, a liquid supplying pump 140, and a liquid supplying flow path 141.

The liquid supplying flow path 141 is connected to a treatment tank 109 in the treatment liquid production unit 100 via the liquid supplying pump 140. By the liquid supplying pump 140, new tap water is supplied from the liquid supplying flow path 141 to the treatment tank 109.

An operation of the control unit 200 will be particularly described below.

The control unit 200 controls the whole of the treatment liquid production device 10C. The control unit 200 controls a pulse power supply 101 and controls water supply and treatment under a prescribed condition. Specifically, the control unit 200 makes a plasma generating device 120 of the treatment liquid production unit 100 generate plasma, and, then, controls the liquid supplying pump 140 to supply only a predefined quantity of new tap water from the liquid supplying flow path 141 to the treatment tank 109. The control unit 200 also controls the plasma generating device 120 to generate plasma again in the treatment water, with which the new tap water is mixed, in the treatment tank 109.

The control unit 200, before controlling the liquid supplying pump 140 to supply new tap water to the treatment tank 109, controls a discharge pump 116 to discharge a portion of the treatment water in the treatment tank 109 from a discharge flow path 115. At this time, new tap water is mixed with at least a small quantity of treatment water in the treatment tank 109. Alternatively, the control unit 200, while controlling the liquid supplying pump 140 to supply new tap water to the treatment tank 109, may control the discharge pump 116 to discharge a portion of the liquid in the treatment tank 109 from the discharge flow path 115.

The control unit 200, before controlling the liquid supplying pump 140 to supply new tap water to the treatment tank 109, may make the plasma generating device 120 stop generating plasma.

Figure 11:
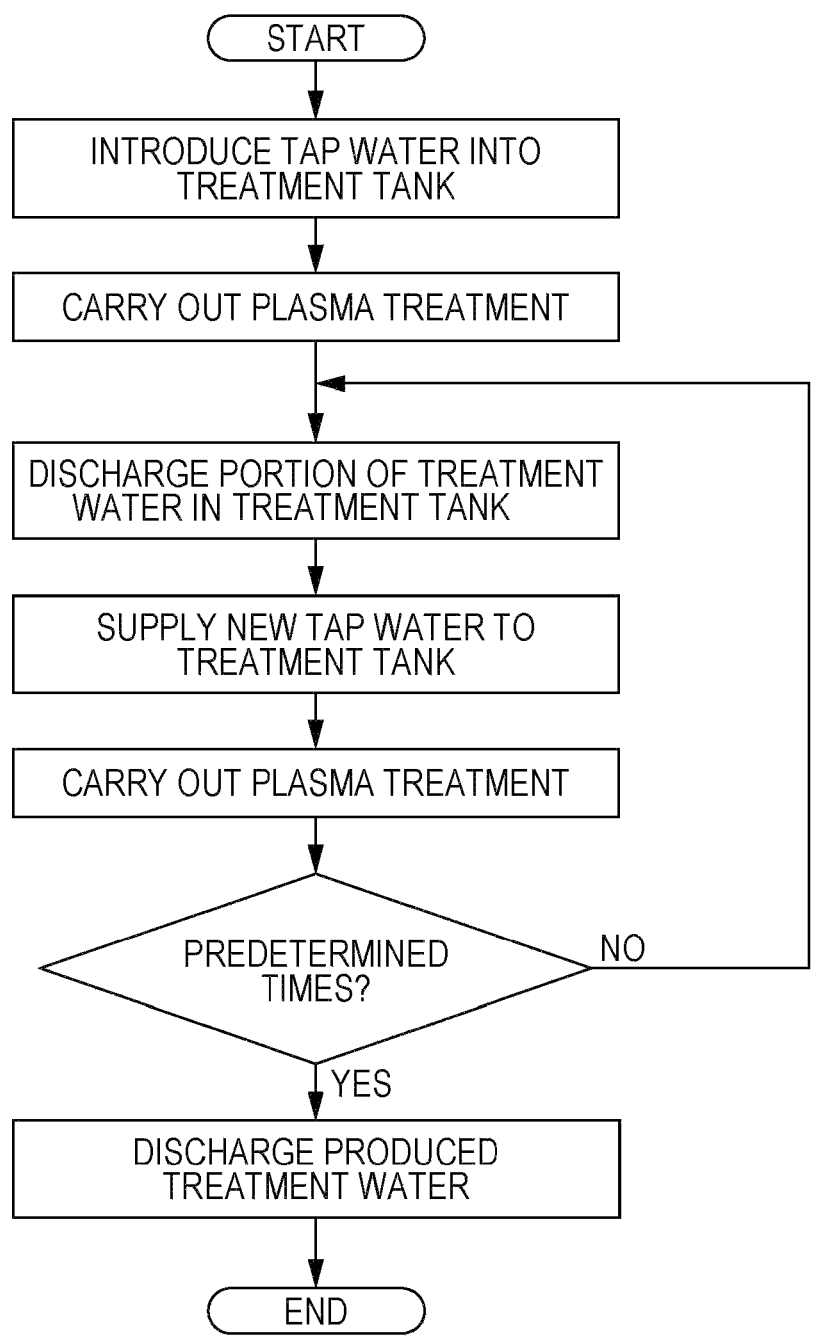
FIG. 11 is an exemplary flowchart illustrating a treatment liquid production method according to the second embodiment.

It is also possible to prescribe the operations of the control unit 200 described above as a treatment liquid production method. FIG. 11 illustrates an example of a process flow of the treatment liquid production method according to the second embodiment.

First, tap water is introduced into the treatment tank 109.

Next, a gas bubble is formed in the tap water in the treatment tank 109, and plasma is generated in the gas bubble.

Then, a portion of treatment water in the treatment tank 109 is discharged and made to be in contact with a target.

Next, new tap water is introduced into the treatment tank 109, a gas bubble is formed in the mixed water, into which the new tap water is mixed, in the treatment tank 109, and plasma is generated in the gas bubble.

Thereafter, a step in which a portion of the treatment water is discharged and made to be in contact with the target, a step in which new tap water is introduced, and a step in which a gas bubble is formed in the mixed water and plasma is generated in the gas bubble are repeated in this order.

Generating of plasma may be stopped before new tap water is supplied to the treatment tank 109 or before the treatment water is discharged from the treatment tank 109.

Figure 12:
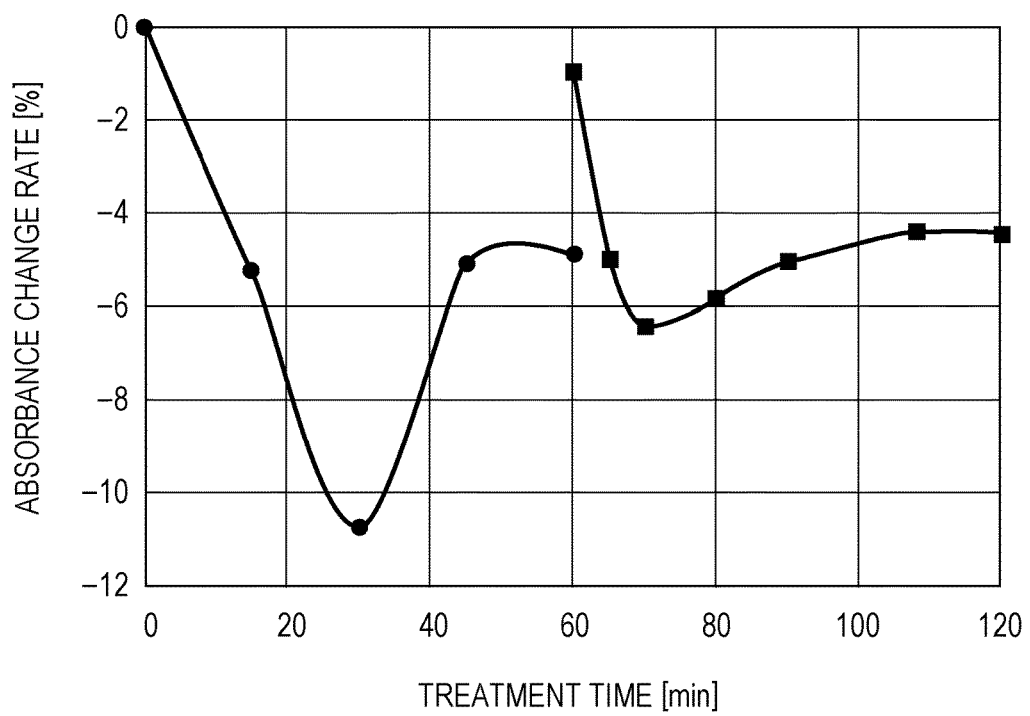
FIG. 12 is a graph illustrating a relation between accumulated treatment time and the initial oxidizing power of the treatment liquid production device.

Referring to FIG. 12, characteristics of treatment water produced by the treatment liquid production device 10C will be described.

FIG. 12 is a graph illustrating a relation between accumulated treatment time by the treatment liquid production device 10C and the initial oxidizing power. In FIG. 12, the horizontal axis represents the accumulated treatment time and the vertical axis represents an absorbance change rate.

In FIG. 12, as with FIG. 5, a result obtained by evaluating decoloration of an indigo carmine aqueous solution when treatment water was made to react with the indigo carmine aqueous solution is illustrated. Specifically, 20 µL of a 1000 ppm indigo carmine aqueous solution and 1.98 mL of treatment water were prepared. The indigo carmine aqueous solution and the treatment water were mixed and stirred. When 30 seconds had passed thereafter, the absorbance of light with a wavelength of 610 nm (initial oxidizing power) was measured by using an ultraviolet-visible spectrophotometer.

First, in the first half of treatment, treatment of 300 mL of tap water was carried out for 60 minutes by using the pulse power supply 101 with an input of 30 W to produce treatment water. Then, operation of the plasma generating device 120 was stopped once. Thereafter, in the last half of treatment, treatment water equivalent to a half of the capacity of the treatment tank 109 was discharged from the treatment tank 109, the same quantity of new tap water was added as a replacement, and plasma was generated in the mixed water by starting the operation of the plasma generating device 120 again. Every predetermined interval, the oxidizing power of sampled treatment water was evaluated by the above-described method. Data obtained in the first half of treatment are plotted with circles, and data obtained in the last half of treatment are plotted with squares.

As illustrated in FIG. 12, as with FIG. 5, a tendency in which the initial oxidizing power increased rapidly in an initial phase of treatment, had a first peak soon, and decreased gradually was confirmed. After the treatment water was replaced, the initial oxidizing power significantly decreased. Thereafter, the initial oxidizing power increased rapidly again, had a second peak soon, and decreased gradually. A tendency in which the initial oxidizing power became substantially constant in the end was confirmed.

It is possible to adjust the emerging positions and amounts of the first and second peaks in FIG. 12 by appropriately adjusting the quantity of treatment water to be replaced. In consequence, treatment water having a characteristic in which the initial oxidizing power thereof has successive peaks is obtained. It is possible to implement a treatment liquid production device that is capable of producing treatment water having a high initial oxidizing power even when the treatment time changes to some extent.

The slope of a curve reaching the second peak is steeper than the slope of a curve reaching the first peak. This fact means that it is possible to produce treatment water having a high initial oxidizing power rapidly. Leaving a portion of treatment water after treatment in the treatment tank 109 and adding new tap water make it possible to significantly shorten the time for the initial oxidizing power to reach a peak, compared with the case in which the operation of the plasma generating device 120 is started again after the treatment tank 109 is emptied completely and new tap water is prepared in the treatment tank 109.

With the second embodiment, it is possible to significantly shorten the time to produce treatment water, that is, the time for plasma treatment.

Third Embodiment

A treatment liquid production device 10D according to a third embodiment will be described.

A configuration of the treatment liquid production device 10D is substantially the same as the configuration of the treatment liquid production device 10C according to the second embodiment illustrated in FIG. 10. Thus, the configuration of the treatment liquid production device 10D will be described referring to FIG. 10. The treatment liquid production device 10D includes a treatment liquid production unit 100, a control unit 200, a liquid supplying pump 140, and a liquid supplying flow path 141. An operation of the control unit 200 will be particularly described below.

The treatment liquid production device 10D differs from the treatment liquid production device 10C according to the second embodiment in that, in producing treatment water, the treatment liquid production device 10D does not discharge the treatment water produced in the treatment tank 109. The treatment liquid production device 10D introduces a small quantity of tap water into the treatment tank 109, and, then, starts operating a plasma generating device 120. Thereafter, the treatment liquid production device 10D, without discharging the treatment water, introduces a small quantity of new tap water again and makes the plasma generating device 120 operate. These operations are repeated the predetermined number of times.

The control unit 200 controls the whole of the treatment liquid production device 10D. The control unit 200, by controlling a pulse power supply 101, controls water supply and treatment under a prescribed condition. Specifically, the control unit 200, after making the plasma generating device 120 generate plasma, controls the liquid supplying pump 140 to supply only a predefined quantity of new tap water from the liquid supplying flow path 141 to the treatment tank 109. In consequence, the quantity of a liquid in the treatment tank 109 increases. The control unit 200 also controls the plasma generating device 120 to generate plasma again in the treatment water, with which the new tap water is mixed, in the treatment tank 109.

The control unit 200 may, before controlling the liquid supplying pump 140 to supply new tap water to the treatment tank 109, make the plasma generating device 120 stop generating plasma.

It is also possible to prescribe the operations of the control unit 200 described above as a treatment liquid production method.

Figure 13:
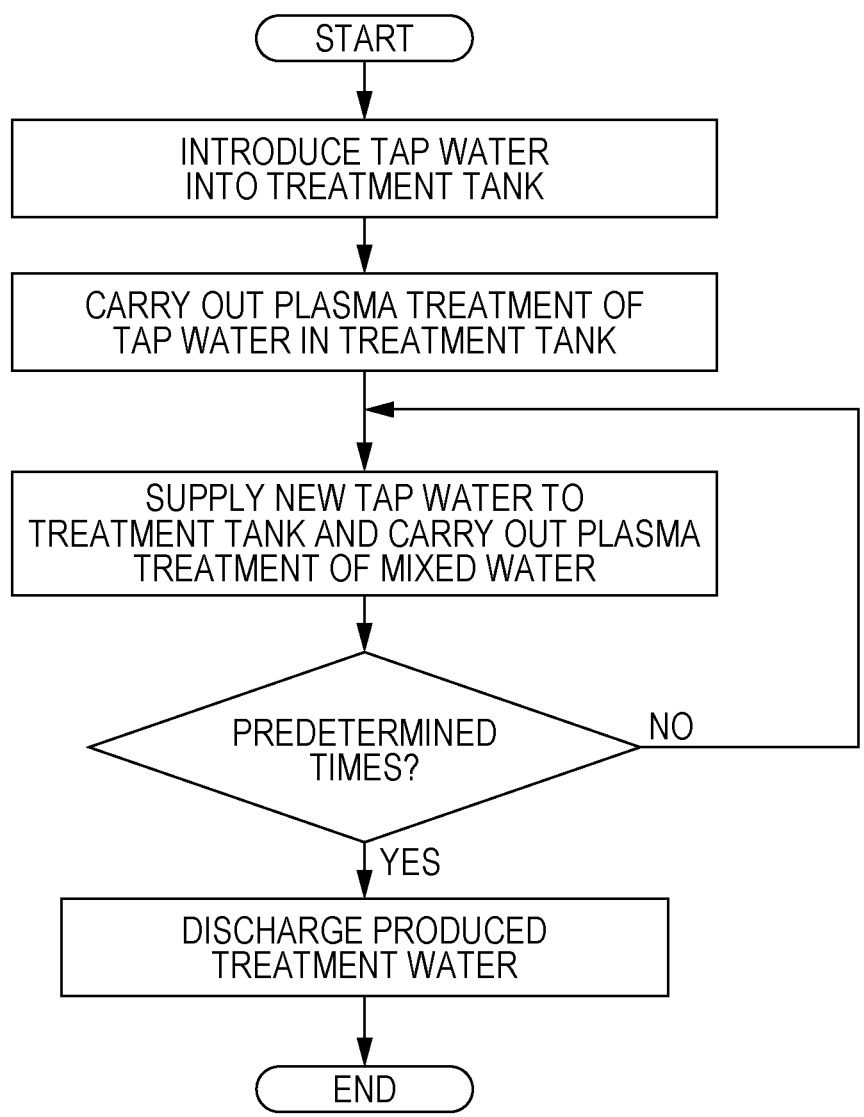
FIG. 13 is an exemplary flowchart illustrating a treatment liquid production method according to a third embodiment.

FIG. 13 illustrates an example of a process flow of the treatment liquid production method according to the third embodiment.

First, tap water is introduced into the treatment tank 109.

Next, a gas bubble is formed in the tap water in the treatment tank 109, and plasma is generated in the gas bubble.

New tap water is supplied to the treatment tank 109, a gas bubble is formed in mixed water, into which the new tap water is mixed, in the treatment tank 109, and plasma is generated in the gas bubble. These operations are repeated the predetermined number of times.

Generating of plasma may be stopped before new tap water is supplied to the treatment tank 109.

Last, the produced treatment water is discharged from a discharge flow path 115.

Figure 14:
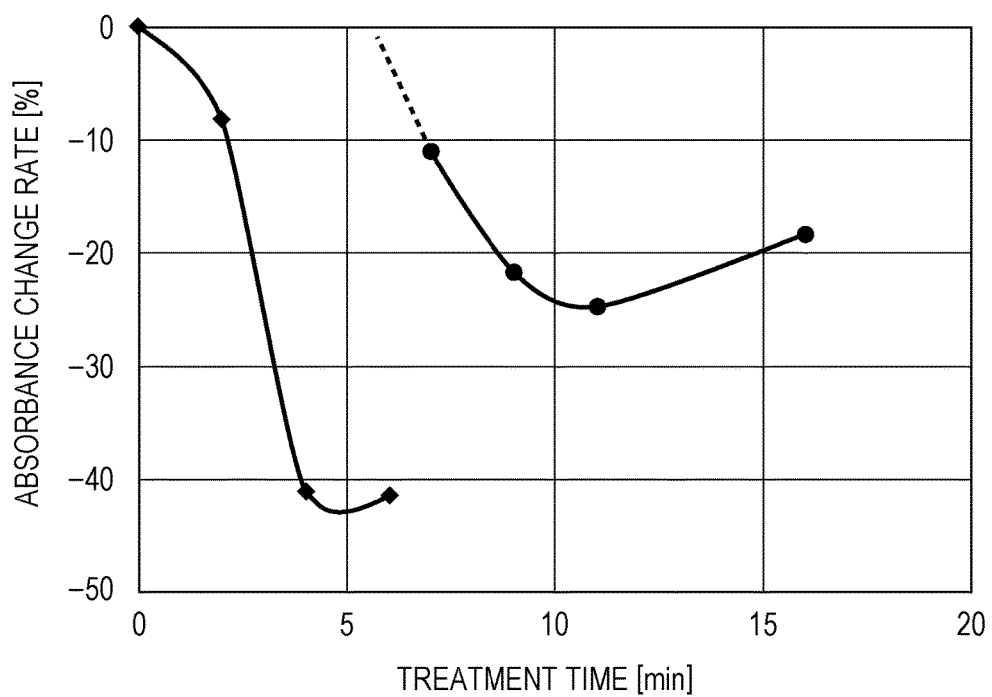
FIG. 14 is a graph illustrating a relation between accumulated treatment time and the initial oxidizing power of the treatment liquid production device.

Referring to FIG. 14, characteristics of treatment water produced by the treatment liquid production device 10D will be described.

FIG. 14 is a graph illustrating a relation between accumulated treatment time by the treatment liquid production device 10D and the initial oxidizing power. In FIG. 14, the horizontal axis represents the accumulated treatment time and the vertical axis represents an absorbance change rate.

By repeating twice a series of operations of introducing 60 mL of tap water into the treatment tank 109 and producing treatment water, 120 mL of treatment water was produced. In FIG. 14, as with FIG. 5, a result obtained by evaluating decoloration of an indigo carmine aqueous solution when the treatment water was made to react with the indigo carmine aqueous solution is illustrated.

It has been confirmed by experiment that, when treatment of several 100 mL of tap water is carried out in plasma treatment using the plasma generating device 120, the time from the start of treatment to the emergence of a peak value of the initial oxidizing power is proportional to the quantity of treatment liquid the plasma treatment produces. From this fact, it is thought that, in a case of, for example, 60 mL of tap water, a peak value of the initial oxidizing power is attained when 6 minutes have passed since the start of operation of the plasma generating device 120. However, the experimental result illustrated in FIG. 14 shows that, in a case of 60 mL of treatment water, a peak value was attained in 5 minutes. In other words, a tendency in which, by carrying out treatment of a small quantity of tap water, the time for the initial oxidizing power to take a peak value is shortened is confirmed. Accordingly, when the quantity of used treatment water per use is as small as, for example, several 10 mL, it is advantageous to carry out treatment for the several 10 mL of treatment water even if required electric power consumption or the like is taken into consideration.

The second peak point in this experiment was reached in 5 minutes after the first peak. It is thought that, by a method in which 120 mL of tap water is treated collectively, it takes about 12 minutes to attain a peak characteristic. Compared with this conventional method, it is possible to shorten the treatment time by about 15% by using the treatment liquid production device 10D.

Furthermore, by the treatment liquid production device 10D, leaving a portion of treatment water in the treatment tank 109 and adding new tap water make it possible to significantly shorten the time for the initial oxidizing power to reach a peak, compared with the case in which the operation of the plasma generating device 120 is started after the treatment tank 109 is emptied completely and new tap water is prepared in the treatment tank 109.

With the third embodiment, it is possible to significantly shorten the time to produce treatment water, that is, the time for plasma treatment, and to maintain a high oxidizing power.

Fourth Embodiment

A treatment liquid production device 10E according to a fourth embodiment will be described.

A configuration of the treatment liquid production device 10E is substantially the same as the configuration of the treatment liquid production device 10C according to the second embodiment illustrated in FIG. 10. Thus, the configuration of the treatment liquid production device 10E will be described referring to FIG. 10. The treatment liquid production device 10E includes a treatment liquid production unit 100, a control unit 200, a liquid supplying pump 140, and a liquid supplying flow path 141. An operation of the control unit 200 will be particularly described below.

The treatment liquid production device 10E, without introducing new tap water into the treatment tank 109, reuses treatment water in the treatment tank 109. In view of this point, the treatment liquid production device 10E differs from the treatment liquid production device 10C according to the second embodiment. It is assumed that, in the treatment liquid production device 10E, after only a predetermined quantity of treatment water has been used from the whole treatment water filling the treatment tank 109, a sufficient quantity of treatment water for a single use is left in the treatment tank 109. In this case, the treatment liquid production device 10E keeps the treatment water as it is, and makes the plasma generating device 120 operate again in using the treatment water. That is, the treatment liquid production device 10E produces treatment water again by reusing treatment water.

The control unit 200, after making the plasma generating device 120 generate plasma, makes the plasma generating device 120 stop generating plasma once. Then, when a predetermined time has passed, the control unit 200 makes the plasma generating device 120 generate plasma again.

It is also possible to prescribe the operations of the control unit 200 described above as a treatment liquid production method.

Figure 15:
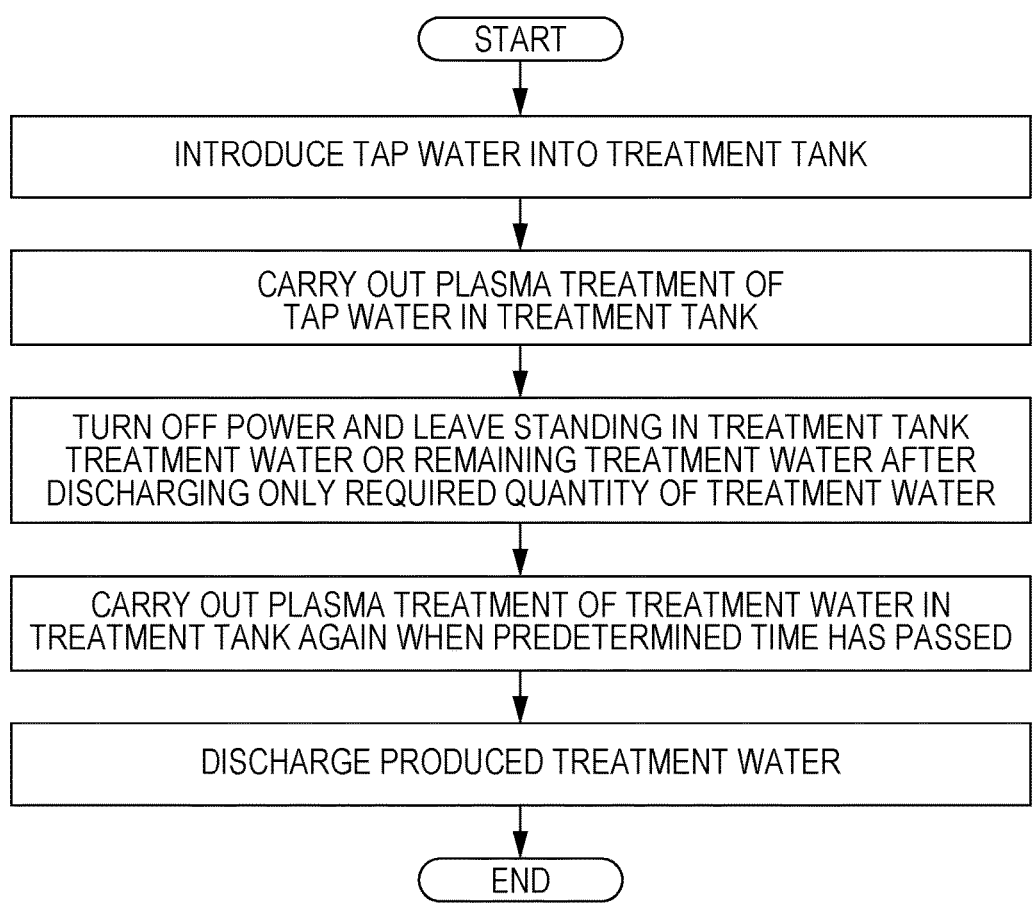
FIG. 15 is an exemplary flowchart illustrating a treatment liquid production method according to a fourth embodiment.

FIG. 15 illustrates an example of a process flow of the treatment liquid production method according to the fourth embodiment.

First, tap water is introduced into the treatment tank 109.

Next, treatment water is produced by forming a gas bubble in the tap water in the treatment tank 109 and generating plasma in the gas bubble.

Next, the generating of plasma is stopped once, and the produced treatment water or treatment water remaining after a portion of the treatment water has been discharged is left standing.

When a predetermined time has passed, a gas bubble is formed in the treatment water in the treatment tank 109 again, plasma is generated in the gas bubble again, and treatment water is produced again.

Last, the produced treatment water is discharged from a discharge flow path 115.

Figure 16:
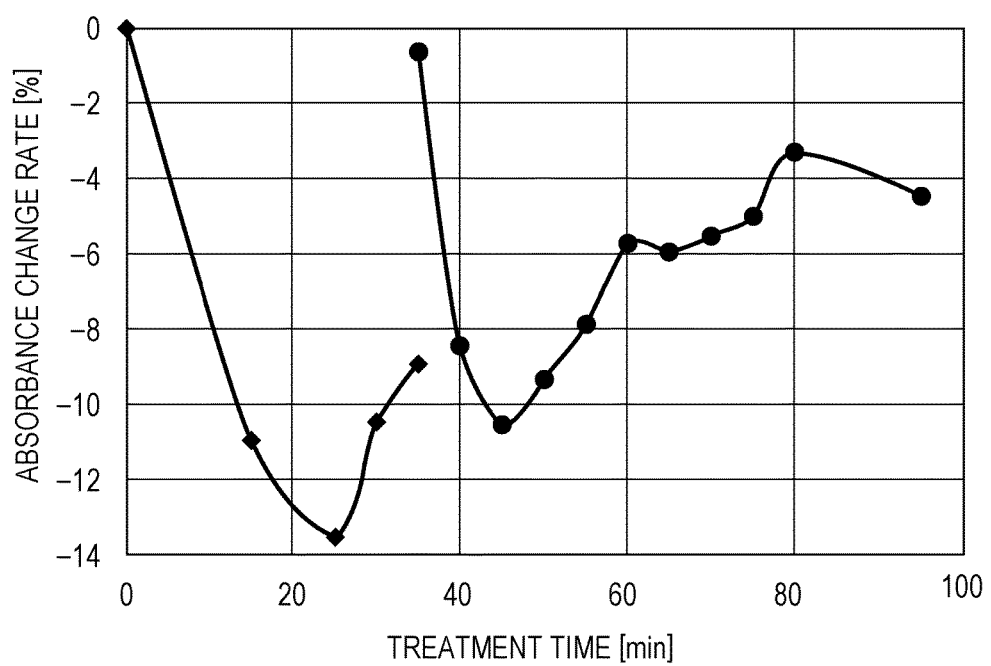
FIG. 16 is a graph illustrating a relation between accumulated treatment time and the initial oxidizing power of a treatment liquid production device.

Referring to FIG. 16, characteristics of treatment water produced by the treatment liquid production device 10E will be described.

FIG. 16 is a graph illustrating a relation between accumulated treatment time by the treatment liquid production device 10E and the initial oxidizing power. In FIG. 16, the horizontal axis represents the accumulated treatment time and the vertical axis represents an absorbance change rate.

In FIG. 16, as with FIG. 5, a result obtained by evaluating decoloration of an indigo carmine aqueous solution when the treatment water was made to react with the indigo carmine aqueous solution is illustrated. Specifically, 20 µL of a 1000 ppm indigo carmine aqueous solution and 1.98 mL of treatment water were prepared. The indigo carmine aqueous solution and the treatment water were mixed and stirred. When 30 seconds had passed thereafter, the absorbance of light with a wavelength of 610 nm was measured by using an ultraviolet-visible spectrophotometer.

First, in the first half of treatment, treatment of 300 mL of tap water was carried out for 35 minutes by using the pulse power supply 101 with an input of 30 W to produce treatment water. In the last half of treatment, after the treatment water had been left standing in the treatment tank 109 for a day, the plasma generating device 120 was operated again. Every predetermined interval, the initial oxidizing power of sampled treatment water was evaluated by the above-described method. Data obtained in the first half of treatment are plotted with circles, and data obtained in the last half of treatment after the treatment water being left standing are plotted with squares.

As illustrated in FIG. 16, as with FIG. 5, a tendency in which the initial oxidizing power increased rapidly in an initial phase of treatment, had a first peak soon, and decreased gradually was confirmed. It was confirmed that, because the operation was stopped thereafter, the oxidizing power had almost disappeared a day later.

However, by restarting the operation from that state, the initial oxidizing power recovered rapidly at a rate higher than the rate at which the initial oxidizing power of treatment water produced in a previous day had increased. At the same time, it is possible to produce treatment water having almost the same initial oxidizing power as before the stop of operation in about 5 minutes. It was also confirmed that the required time to reach a peak point had decreased to approximately a half of the corresponding time required in the treatment the previous day. In this way, by stopping plasma treatment of treatment water once and carrying out plasma treatment of the treatment water again after a certain time has passed, it is possible to produce treatment water having a high initial oxidizing power in a short time compared with a case of newly producing treatment water. Although the result exemplified in FIG. 16 shows that the initial oxidizing power at the second peak point is about three quarters lower than the initial oxidizing power at the first peak point, the treatment water for which plasma treatment is carried out again still has a sufficient treatment capability.

In the fourth embodiment, an example in which treatment water is produced by carrying out plasma treatment again a day later was described. However, the present disclosure is not limited to the example, and, the shorter the downtime to the second plasma treatment is, the shorter the time required for the initial oxidizing power of treatment water to recover becomes. When a long downtime leading to a reduction in power consumption is taken into consideration, it is possible to achieve a low electric power consumption more surely if the downtime is not less than 100 times of a cycle of a pulse signal applied between electrodes.

With the fourth embodiment, it is possible to significantly reduce the treatment time to attain an initial oxidizing power value close to a peak value.

(Variation)

Figure 17:
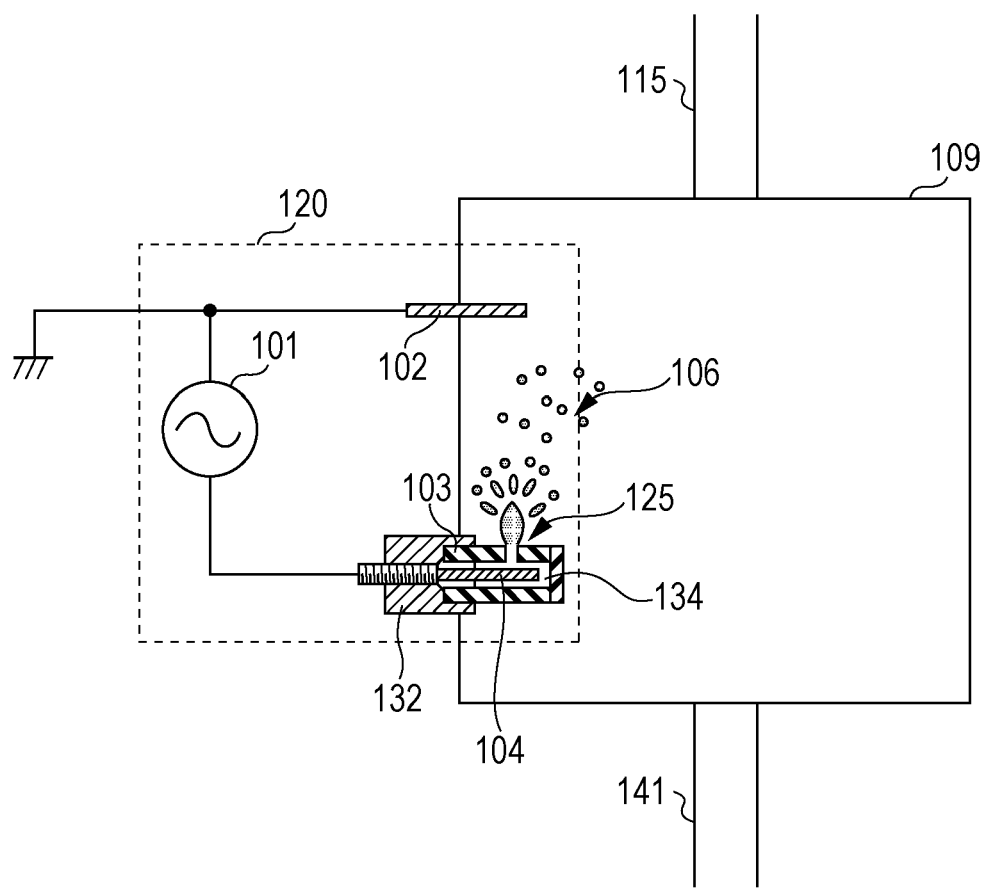
FIG. 17 is an overall configuration diagram illustrating a treatment liquid production unit according to a variation.
Figure 18:
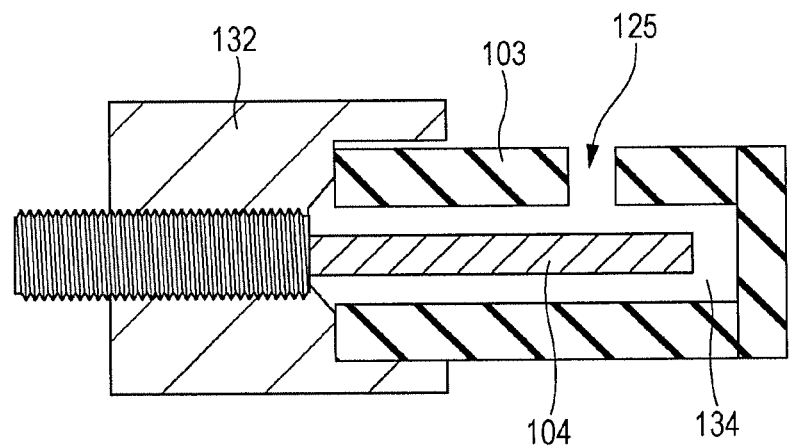
FIG. 18 is a cross-sectional view illustrating a configuration of electrodes around a first metal electrode.
Figure 19:
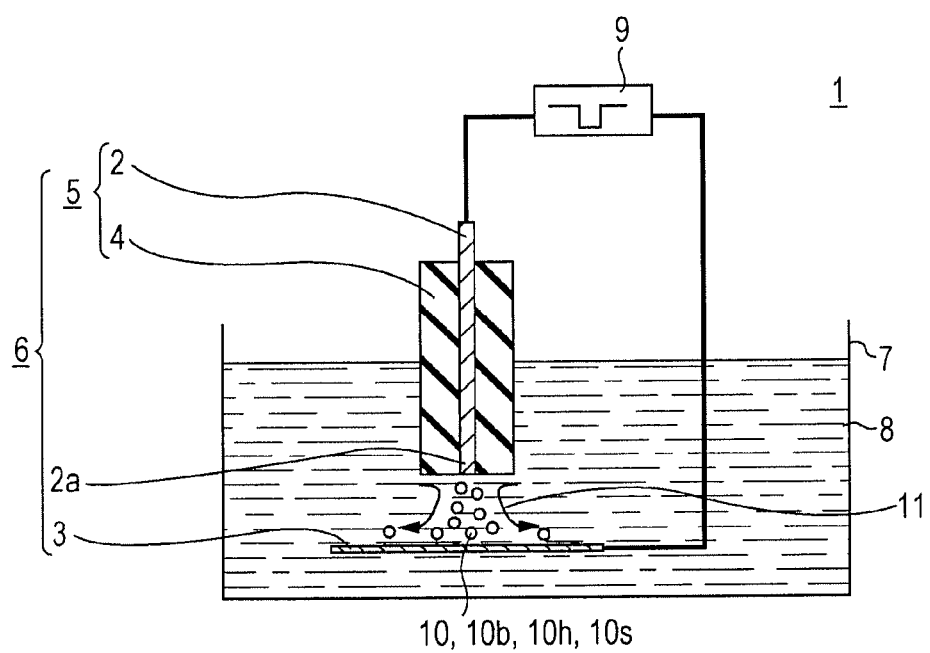
FIG. 19 is an overall configuration diagram illustrating a conventional liquid treatment device.

The configuration of the plasma generating device 120 of the present disclosure is not limited to the configurations described above. Referring to FIGS. 17 and 18, a variation of the plasma generating device 120 will be described below.

The plasma generating device 120 according to the variation differs from the plasma generating device of the first embodiment in the configuration of electrodes. Furthermore, the plasma generating device 120 according to the variation differs from the plasma generating device of the first embodiment in that the plasma generating device 120 generates gas in a liquid by vaporizing treatment water as a substitution for supplying gas by using an gas flow pump. Other components of both devices are identical, and description thereof will be omitted. The configuration of electrodes in the plasma generating device 120 will be particularly described below.

FIG. 17 is an overall configuration diagram illustrating a treatment liquid production unit 100 according to the variation. FIG. 18 is a schematic cross-sectional view illustrating a configuration of electrodes around a first metal electrode 104.

The diameter of the opening section 125 of the insulating body 103 is 1 mm in the first embodiment. Electric field strength is inversely proportional to the square of a diameter. Thus, the smaller the diameter is, the higher the electric field strength becomes. Therefore, in terms of electric field strength, it is desirable to have a small diameter. However, in the first embodiment, it is also necessary to make the diameter of the first metal electrode 104 small at the same time, making it difficult to manufacture the first metal electrode 104. When the diameter of the first metal electrode 104 becomes small, an electric discharge becomes intense at a tip portion of the electrode, causing a large abrasion on the electrode.

An example of a structure of electrodes, which, to avoid such a problem, makes it possible to intensify electric field strength without making the diameter of the first metal electrode 104 small, will be described below.

The plasma generating device 120 includes a first metal electrode 104, an insulating body 103, a second metal electrode 102, and a holding block 132.

In the surrounding area of the first metal electrode 104, the insulating body 103 is arranged so as to form a space 134. The insulating body 103 has at least one opening section 125 which interconnects the inside of a treatment tank 109 and the space 134. Treatment water 110 in the treatment tank 109 intrudes from this opening section 125, and the space 134 is filled with the treatment water 110. One ends of the first metal electrode 104 and the insulating body 103 are fixed to the holding block 132 individually. It is sufficient to arrange the second metal electrode 102 to any position in the treatment tank 109, and the position for the arrangement is not limited to any specific position.

At least a portion of the first metal electrode 104 is arranged inside the treatment tank 109 which is filled with treatment water. The first metal electrode 104 has a cylindrical shape with a diameter of, for example, 2 mm. The first metal electrode 104 may have a diameter larger than 2 mm. The shape of the first metal electrode 104 is not limited to a cylindrical shape, and may be, for example, an arbitrary shape, such as a cubic shape and a planar shape. A material of which the first metal electrode 104 is made may be, for example, iron, tungsten, copper, aluminum, platinum, or an alloy including one or a plurality of metals selected therefrom.

At least a portion of the second metal electrode 102 is also arranged inside the treatment tank 109 which is filled with treatment water. It is sufficient that the second metal electrode 102 is made of a conductive metal material. For example, as with the first metal electrode 104, the second metal electrode 102 may be made of a material, such as iron, tungsten, copper, aluminum, platinum, or an alloy including one or a plurality of metals selected therefrom.

The insulating body 103 is arranged so as to form the space 134 around the first metal electrode 104. To the insulating body 103, the opening section 125 which interconnects the inside of the treatment tank 109 and the space 134 is formed. The insulating body 103 has a cylindrical shape with an internal diameter of 3 mm and an external diameter of 5 mm, and has the opening section 125 with a diameter of 0.7 mm. The insulating body 103 may have an arbitrary size and an arbitrary shape as long as the insulating body 103 forms the space 134 around the first metal electrode 104. The diameter of the opening section 125 may take an arbitrary value less than or equal to, for example, 2 mm. A plurality of opening sections 125 may be formed. The position at which the opening section 125 is formed may be, for example, on the upper side face of the insulating body 103, as illustrated in FIG. 17. Directing the opening direction of the opening section 125 upward in this way makes it possible to prevent the opening section 125 from becoming clogged with a gas bubble 106. A material of which the insulating body 103 is made may be, for example, aluminum oxide, magnesium oxide, yttrium oxide, insulating plastic, glass, quartz, or the like.

The holding block 132 is connected to respective one ends of the first metal electrode 104 and the insulating body 103. Connection portions between the holding block 132 and each of the first metal electrode 104 and the insulating body 103 may have a sealing structure to prevent treatment water from leaking out. For example, the structure may be a structure in which the first metal electrode 104 and the insulating body 103 are screwed to the holding block 132. The sealing structure is not limited to this structure and may be an arbitrary structure.

A power supply 101 applies a high voltage of 4 to 10 kV with a frequency of 1 to 100 kHz between the first metal electrode 104 and the second metal electrode 102. The power supply 101 may apply a pulse voltage or an alternating voltage. A voltage waveform may be, for example, any one of a pulse, a half sine wave, and a sine wave. Too much current causes electric power to be used in such a way as to heat not only treatment water in the space 134 but also the whole treatment water in the treatment tank 109. Consequently, efficiency of plasma generating actually decreases. Thus, in the variation, the current value is set at 3 A or less.

If the current value is less than 1 mA, it needs time to vaporize treatment water in the space 134. Consequently, it is desirable that the current value is set at a value in a range from 1 mA to 3 A.

[Operation]

The space 134 formed between the first metal electrode 104 and the insulating body 103 is filled with the treatment water 110 before plasma treatment starts. Starting from this state, by applying a voltage between the first metal electrode 104 and the second metal electrode 102 from the power supply 101, the treatment water in the space 134 is heated.

Due to electric power input from the first metal electrode 104, the temperature of the treatment water in the space 134 rises. Due to this temperature rise, the treatment water in the space 134 is vaporized, and gas is generated. This gas groups together in the space 134 to form a mass. Then, this mass of gas is released into the treatment water 110 in the treatment tank 109 from the opening section 125 formed on the insulating body 103 by a pressure difference between pressure inside the space 134 and pressure in the treatment tank 109.

When this mass of gas passes the opening section 125, treatment water existing in the opening portion is replaced with the gas. With this process, the first metal electrode 104 and the second metal electrode 102 are insulated from each other. At this time, an electric field is concentrated to the mass of gas existing around the opening section 125 to generate an electric discharge. As a result, plasma is generated in the mass of gas. Once plasma is generated, plasma keeps being generated consecutively and continuously. Then, the mass of gas containing plasma is released into the treatment water 110 in the treatment tank 109 from the opening section 125. Then, the plasma comes to project from the opening section 125 into the treatment water 110 in the treatment tank 109.

Further, portions of the mass of gas containing plasma separate to form a plurality of gas bubbles 106. The gas bubbles 106 spread out in the treatment water 110 in the treatment tank 109. The plurality of gas bubbles 106 contain bubbles with micrometer and sub-micrometer diameters.

As described above, the plasma generating device 120 according to the variation has a function to create microbubbles. The gas bubbles 106 differ from normal microbubbles in that electrons, ions, or radicals generated by plasma are contained therein.

A treatment liquid production device according to the present disclosure is useful as a water purification device or the like for waste water treatment or the like.

What is claimed is:

1. A treatment liquid production device comprising:
    a first tank;
    a first plasma generating device that includes a first pair of electrodes and a first power supply, the first power supply applying a voltage between the first pair of electrodes, the first plasma generating device generating plasma in a liquid in the first tank;
    a second tank;
    a second plasma generating device that includes a second pair of electrodes and a second power supply, the second power supply applying a voltage between the second pair of electrodes, the second plasma generating device generating plasma in a liquid in the second tank; and
    a controller configured to:
        cause the first plasma generating device to generate plasma during a first period to produce a first treatment liquid in the first tank; and
        cause the second plasma generating device to generate plasma during a second period to produce a second treatment liquid in the second tank, the second period being longer than the first period, an initial oxidizing power of the first treatment liquid being higher than an initial oxidizing power of the second treatment liquid, a remaining oxidizing power of the second treatment liquid being higher than a remaining oxidizing power of the first treatment liquid.

2. The treatment liquid production device according to claim 1, wherein
    the first period is substantially identical to a time at which, on a graph that indicates a relation between a plasma treatment time of the first plasma generating device and the initial oxidizing power of the first treatment liquid, the initial oxidizing power is a maximum value at a peak, and
    the second period is identical to a time at which, on a graph that indicates a relation between a plasma treatment time of the second plasma generating device and the initial oxidizing power of the second treatment liquid, the initial oxidizing power is a substantially saturated value.

3. The treatment liquid production device according to claim 1, further comprising:
    a discharge flow path connected to the first tank and the second tank; and
    at least one discharge pump provided to the discharge flow path, the at least one discharge pump discharging the first treatment liquid in the first tank and the second treatment liquid in the second tank to the outside via the discharge flow path, wherein
    the controller causes the at least one discharge pump to discharge the first treatment liquid and the second treatment liquid to the outside via the discharge flow path at the same time.

4. The treatment liquid production device according to claim 1, further comprising:
    a discharge flow path connected to the first tank and the second tank; and
    at least one discharge pump provided to the discharge flow path, the at least one discharge pump discharging the first treatment liquid in the first tank and the second treatment liquid in the second tank to the outside via the discharge flow path, wherein
    the controller causes the at least one discharge pump to discharge the first treatment liquid and the second treatment liquid individually to the outside via the discharge flow path.

5. A treatment liquid production device comprising:
    a first tank;
    a plasma generating device that includes a pair of electrodes and a power supply, the power supply applying a voltage between the pair of electrodes, the plasma generating device generating plasma in a liquid in the first tank;
    a second tank;
    a connection flow path that connects the first tank and the second tank;
    a connection pump provided to the connection flow path; and
    a controller configured to:
        cause the plasma generating device to generate plasma during a second period to produce a second treatment liquid in the first tank;

cause the connection pump to move the second treatment liquid in the first tank to the second tank via the connection flow path; and cause the plasma generating device to generate plasma during a first period to produce a first treatment liquid in the first tank, the first period being longer than the second period, an initial oxidizing power of the first treatment liquid being higher than an initial oxidizing power of the second treatment liquid, a remaining oxidizing power of the second treatment liquid being higher than a remaining oxidizing power of the first treatment liquid.

6. The treatment liquid production device according to claim 5, wherein the first period is substantially identical to a time at which, on a graph that indicates a relation between a plasma treatment time of the plasma generating device and the initial oxidizing power of the first treatment liquid, the initial oxidizing power is a maximum value at a peak, and the second period is identical to a time at which, on a graph that indicates a relation between the plasma treatment time of the plasma generating device and the initial oxidizing power of the second treatment liquid, the initial oxidizing power is a substantially saturated value.

7. The treatment liquid production device according to claim 5, further comprising:

a discharge flow path connected to the first tank and the second tank; and at least one discharge pump provided to the discharge flow path, the at least one discharge pump discharging the first treatment liquid in the first tank and the second treatment liquid in the second tank to the outside via the discharge flow path, wherein the controller causes the at least one discharge pump to discharge the first treatment liquid and the second treatment liquid to the outside via the discharge flow path at the same time.

8. The treatment liquid production device according to claim 5, further comprising:

a discharge flow path connected to the first tank and the second tank; and at least one discharge pump provided to the discharge flow path, the at least one discharge pump discharging the first treatment liquid in the first tank and the second treatment liquid in the second tank to the outside via the discharge flow path, wherein the controller causes the at least one discharge pump to discharge the first treatment liquid and the second treatment liquid individually to the outside via the discharge flow path.

* * * * *